(12) United States Patent
Pahara et al.

(10) Patent No.: US 11,926,811 B2
(45) Date of Patent: Mar. 12, 2024

(54) PERSONAL LABORATORY FOR GENETIC ENGINEERING, CULTURING AND ANALYSIS OF MICROORGANISMS AND BIOCHEMICALS

(71) Applicant: Amino Labs North Incorporated, Lethbridge County (CA)

(72) Inventors: Justin Pahara, Lethbridge County (CA); Julie Legault, Lethbridge County (CA)

(73) Assignee: Amino Labs North Incorporated, Lethbridge County (CA)

( * ) Notice: Subject to any disclaimer, the term of this patent is extended or adjusted under 35 U.S.C. 154(b) by 0 days.

(21) Appl. No.: 16/037,152

(22) Filed: Jul. 17, 2018

(65) Prior Publication Data
US 2019/0017008 A1 Jan. 17, 2019

Related U.S. Application Data

(60) Provisional application No. 62/533,318, filed on Jul. 17, 2017.

(51) Int. Cl.
*C12M 3/00* (2006.01)
*C12M 1/00* (2006.01)
(Continued)

(52) U.S. Cl.
CPC ............ *C12M 23/48* (2013.01); *C12M 23/06* (2013.01); *C12M 23/10* (2013.01); *C12M 23/42* (2013.01);
(Continued)

(58) Field of Classification Search
CPC ...... C12M 23/48; C12M 23/06; C12M 23/10; C12M 23/42; C12M 23/44; C12M 23/54;
(Continued)

(56) References Cited

U.S. PATENT DOCUMENTS

| 4,950,166 A | 8/1990 | Williams |
| 5,484,293 A | 1/1996 | Ford et al. |

(Continued)

FOREIGN PATENT DOCUMENTS

| CN | 103852510 A | 6/2014 |
| CN | 107038924 A | 8/2017 |

(Continued)

OTHER PUBLICATIONS

Biotechnology Explorer Microbial Culturing Kit (Catalog# 166-5020EDU) (Year: 2014).*

(Continued)

*Primary Examiner* — Michael L Hobbs
*Assistant Examiner* — Lenora A Abel
(74) *Attorney, Agent, or Firm* — Holzer Patel Drennan

(57) ABSTRACT

A personal laboratory apparatus includes a plurality of life sciences laboratory modules disposed on or in a common housing. The laboratory modules include a cooling station, a heating station, an incubator, a bioreactor, and a removable fluidic cartridge that is fluidly coupled to the bioreactor. The personal laboratory apparatus can be sold as a kit with a wetware kit that includes laboratory hardware and ingredients for performing a genetic-engineering experiment. The wetware kit includes a plurality of test tubes and a pre-measured volume or mass of a plurality of materials, each pre-measured volume or mass disposed in a corresponding test tube.

10 Claims, 24 Drawing Sheets

(51) Int. Cl.
*C12M 1/12* (2006.01)
*C12M 1/22* (2006.01)
*C12M 1/34* (2006.01)
*C12M 1/36* (2006.01)
*G09B 5/06* (2006.01)
*G09B 23/00* (2006.01)

(52) U.S. Cl.
CPC .............. *C12M 23/44* (2013.01); *C12M 23/54* (2013.01); *C12M 41/12* (2013.01); *C12M 41/14* (2013.01); *C12M 41/48* (2013.01); *G09B 5/06* (2013.01); *G09B 23/00* (2013.01)

(58) Field of Classification Search
CPC ...... C12M 41/12; C12M 41/14; C12M 41/48; G09B 5/06; G09B 23/00
USPC ...................................................... 435/286.5
See application file for complete search history.

(56) References Cited

U.S. PATENT DOCUMENTS

| | | | |
|---|---|---|---|
| 5,624,638 A | 4/1997 | Negrotti | |
| 5,813,865 A | 9/1998 | Greenbowe et al. | |
| 5,871,361 A | 2/1999 | Gastle et al. | |
| 6,135,776 A | 10/2000 | Erturk et al. | |
| 6,228,635 B1 * | 5/2001 | Armstrong | C12M 41/00 |
| | | | 435/284.1 |
| 6,261,103 B1 | 7/2001 | Stephens et al. | |
| 6,499,054 B1 | 12/2002 | Hesselink et al. | |
| 6,529,705 B1 | 3/2003 | Keller et al. | |
| 6,813,473 B1 | 11/2004 | Bruker | |
| 6,932,611 B2 | 8/2005 | Shen et al. | |
| 7,270,996 B2 * | 9/2007 | Cannon | C12M 37/00 |
| | | | 435/293.1 |
| 7,476,103 B1 | 1/2009 | Norman | |
| 7,917,349 B2 | 3/2011 | Berger et al. | |
| 8,342,332 B2 | 1/2013 | Alhajri | |
| 9,212,344 B2 * | 12/2015 | Tsumura | C12M 29/10 |
| 9,741,256 B2 | 8/2017 | Akopian et al. | |
| 10,457,983 B2 * | 10/2019 | DeJohn | G01N 21/77 |
| 2002/0147799 A1 | 10/2002 | Alhalabi et al. | |
| 2003/0066026 A1 | 4/2003 | Jaffe | |
| 2004/0121299 A1 | 6/2004 | Rougeau et al. | |
| 2005/0026126 A1 | 2/2005 | Hageman | |
| 2005/0064465 A1 * | 3/2005 | Dettloff | C12Q 1/686 |
| | | | 435/5 |
| 2006/0286606 A1 | 12/2006 | Oliver | |
| 2008/0215705 A1 | 9/2008 | Liu et al. | |
| 2008/0233550 A1 | 9/2008 | Solomon | |
| 2010/0248202 A1 | 9/2010 | Thompson et al. | |
| 2012/0066625 A1 | 3/2012 | Encina et al. | |
| 2013/0045471 A1 | 2/2013 | Gibert et al. | |
| 2013/0224851 A1 * | 8/2013 | Ljungmann | B04B 5/0421 |
| | | | 435/308.1 |
| 2015/0093735 A1 | 4/2015 | Smith | |
| 2016/0217700 A1 | 7/2016 | Zimmer et al. | |
| 2017/0140669 A1 | 5/2017 | Dey et al. | |
| 2017/0363678 A1 | 12/2017 | Zubia et al. | |
| 2018/0053439 A1 | 2/2018 | Philippov et al. | |

FOREIGN PATENT DOCUMENTS

| | | | |
|---|---|---|---|
| EP | 1890144 A2 | 2/2008 | |
| KR | 100512915 | 5/2003 | |
| WO | WO0159159 A2 | 8/2001 | |
| WO | WO02094431 A2 | 11/2002 | |
| WO | WO03003275 A1 | 1/2003 | |
| WO | WO2005024756 A1 | 3/2005 | |
| WO | WO-2010036808 A1 * | 4/2010 | ........ A61B 5/150022 |

OTHER PUBLICATIONS

Biotechnology Explorer Microbial Culturing Kit (Catalog# 166-5020EDU)-with date from the WayBack Machine (Year: 2014).*
Biotechnology Explorer™ Microbial Culturing Kit (Year: 2014).*

* cited by examiner

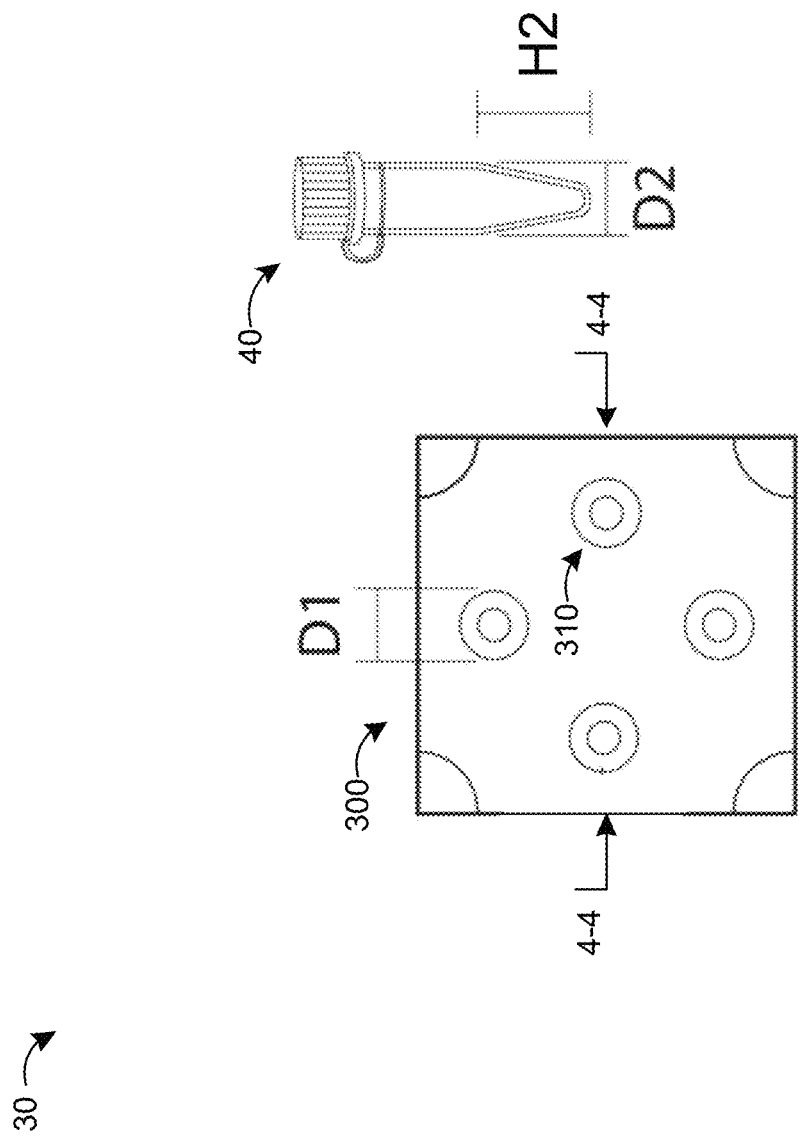

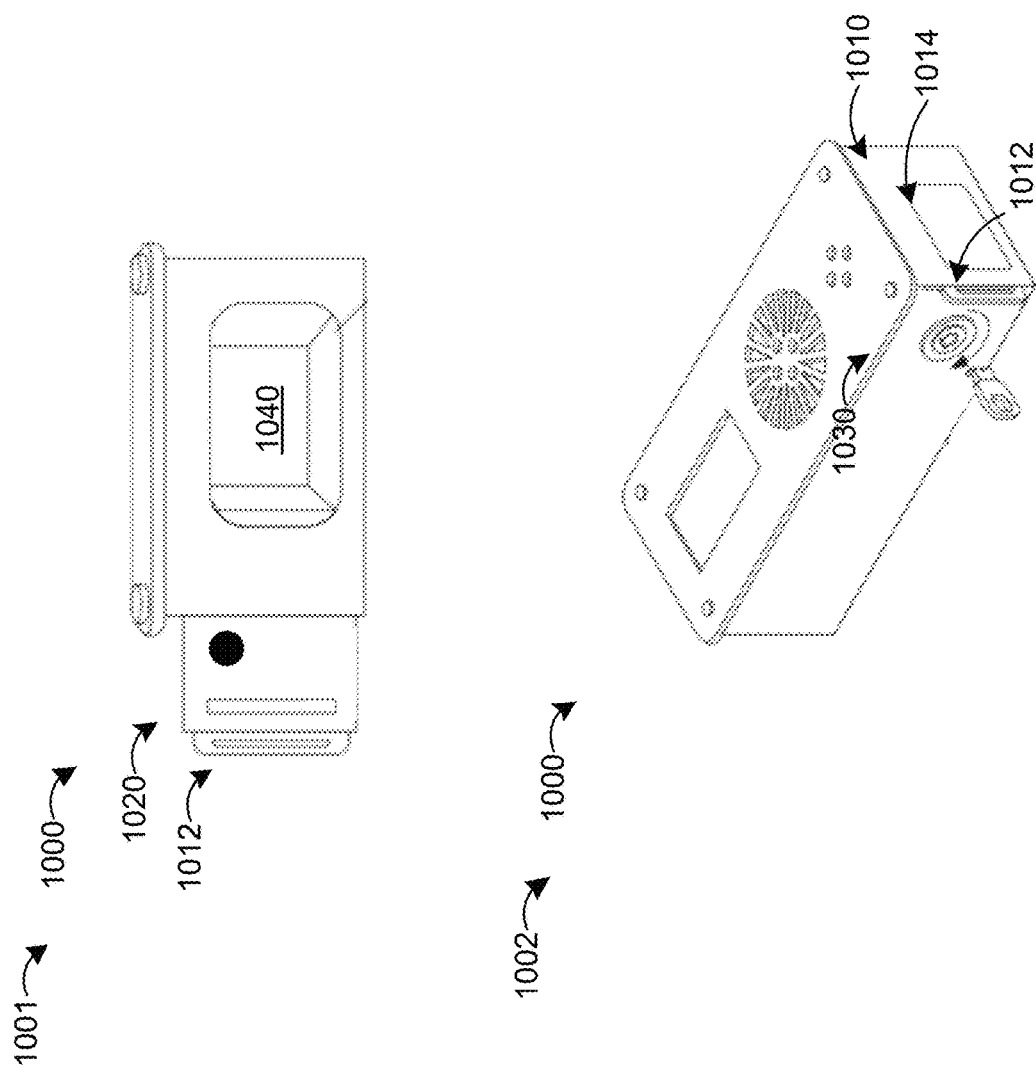

US 11,926,811 B2

PERSONAL LABORATORY FOR GENETIC ENGINEERING, CULTURING AND ANALYSIS OF MICROORGANISMS AND BIOCHEMICALS

RELATED APPLICATIONS

This application claims priority to U.S. Provisional Application No. 62/533,318, titled "Personal Laboratory for Genetic Engineering, Culturing and Analysis of Microorganisms and Biochemicals," filed on Jul. 17, 2017, which is hereby incorporated by reference.

TECHNICAL FIELD

This application is directed to instructional devices for use in hands-on learning of life sciences through the performance of physical experiments, such as experiments involving the engineering and growth of microorganisms.

BACKGROUND

Present day life sciences laboratory equipment for genetic engineering, culturing, analysis and disposal of microorganisms is designed for single purpose communal use, and is therefore typically large and expensive, and built for trained experts. Thus, large budgets, specialized training and numerous pieces of equipment and reagents are typically needed to complete life sciences tasks.

Standard life sciences laboratory practice and equipment involve the use of cooling and heating subsystems, culturing environments, chemical treatment subsystems, and various measurement devices.

The expense, complexity and bulk of standard laboratory equipment and techniques present challenges to those who wish to learn about life sciences "hands-on" through the performance of laboratory experiments and procedures, particularly in the classroom and home settings. In other areas of science and engineering, for example chemistry and electronics, there are available in the market prepackaged sets of equipment and reagents or components to allow a relative beginner to obtain hands-on experience in performing simple chemistry experiments or building simple circuits. However, the biological sciences, and in particular genetic engineering and synthetic biology, lack such practical, affordable or useful and compact bench-top or personal experimentation kits. Thus, there is a need for an apparatus that will substitute for multiple pieces of lab equipment, that is easier to use, that is feasible for use in classroom and home settings with a simple set of reagents and that allows a relative beginner such as a high-school or middle-school student to perform experiments with microorganisms and observe their outcomes.

SUMMARY

Example embodiments described herein have innovative features, no single one of which is indispensable or solely responsible for their desirable attributes. The following description and drawings set forth certain illustrative implementations of the disclosure in detail, which are indicative of several exemplary ways in which the various principles of the disclosure may be carried out. The illustrative examples, however, are not exhaustive of the many possible embodiments of the disclosure. Without limiting the scope of the claims, some of the advantageous features will now be summarized. Other objects, advantages and novel features of the disclosure will be set forth in the following detailed description of the disclosure when considered in conjunction with the drawings, which are intended to illustrate, not limit, the invention.

An aspect of the invention is directed to a personal laboratory apparatus comprising a common housing; a plurality of life sciences laboratory modules disposed on or in the common housing, including: a cooling station; a heating station; an incubator; a bioreactor; and a removable fluidic cartridge that is fluidly coupled to the bioreactor.

In one or more embodiments, the personal laboratory apparatus further comprises a microcontroller in electrical communication with the cooling station, the heating station, the incubator, and the bioreactor. In one or more embodiments, the personal laboratory apparatus further comprises a touch screen disposed on the common housing. In one or more embodiments, the touch screen is in electrical communication with the microcontroller. In one or more embodiments, the microcontroller is configured to send output signals to the touch screen to control a display of the touch screen. In one or more embodiments, the output signals cause the touch screen to display the current temperature of at least one of the cooling station, the heating station, the incubator, and the bioreactor. In one or more embodiments, the touch screen includes user inputs to adjust a temperature set point of at least one of the cooling station, the heating station, the incubator, and the bioreactor.

In one or more embodiments, the bioreactor is disposed in the removable fluid cartridge. In one or more embodiments, the personal laboratory apparatus further comprises a network interface that operably couples the microcontroller to a server.

Another aspect of the invention is directed to a kit comprising a personal laboratory apparatus comprising a common housing; a plurality of life sciences laboratory modules disposed on or in the common housing, including: a cooling station; a heating station; an incubator; a bioreactor; a removable fluidic cartridge that is fluidly coupled to the bioreactor; and a wetware kit comprising laboratory hardware and ingredients for performing a genetic-engineering experiment, the wetware kit comprising: a plurality of test tubes; and a pre-measured volume or mass of a plurality of materials, each pre-measured volume or mass disposed in a corresponding test tube.

In one or more embodiments, the wetware kit further comprises: at least one inoculation loop; a plurality of petri dishes; a capsule comprising a pre-measured mass of a selection agent; and a stencil configured to guide a streaking procedure. In one or more embodiments, the plurality of materials comprises at least one of: sterile water; a growth media; a suspended DNA plasmid; a stab of positive control cells; a transformation or transfection agent; and a recovery media. In some examples, the kit includes a reaction substrate. In other examples, the kit includes an induction substrate that may be on its own, or embedded in or under a fibrous material such as a paper, filter paper, for slow controlled release.

In one or more embodiments, the personal laboratory apparatus further comprises a microcontroller in electrical communication with the cooling station, the heating station, the incubator, and the bioreactor. In one or more embodiments, the personal laboratory apparatus further comprises a touch screen disposed on the common housing, the touch screen in electrical communication with the microcontroller. In one or more embodiments, the microcontroller is configured to send output signals to the touch screen to control a display of the touch screen. In one or more embodiments, the output signals cause the touch screen to display the current temperature of at least one of the cooling station, the heating station, the incubator, and the bioreactor. In one or more embodiments, the touch screen includes user inputs to adjust a temperature set point of at least one of the cooling station, the heating station, the incubator, and the bioreactor.

In one or more embodiments, the bioreactor is disposed in the removable fluid cartridge. In one or more embodiments, the personal laboratory apparatus further comprises a network interface that operably couples the microcontroller to a server. In one or more embodiments, the incubator comprises an incubator chamber sized to receive the petri dishes. In one or more embodiments, the incubator chamber is lockable.

BRIEF DESCRIPTION OF THE DRAWINGS

For a fuller understanding of the nature and advantages of the present concepts, reference is made to the following detailed description of preferred embodiments and in connection with the accompanying drawings, in which:

FIG. 3A is a top view of a test tube holder according to one or more embodiments;

FIG. 10A is a front view and a perspective view of an incubator station according to one or more embodiments;

DETAILED DESCRIPTION

This application discloses a personal laboratory apparatus that both miniaturizes and cohesively combines specialized laboratory equipment used in genetic engineering or synthetic biology. Different embodiments are targeted at different end users. For example, the simplest embodiments can be primarily targeted at non-scientists and novices. More complex embodiments can have more functionality that are sufficient for amateurs or professionals.

Examples of miniaturized stations that are offered in different embodiments include: (a) an ice/ice bucket/ice machine converted into a small station to cool tubes below room temperature; (b) a heating block, water bath, cell incubator, converted into a small station to heat tubes and incubate petri dishes at above room temperature; (c) a shaker incubator or continuous culturing apparatus converted into a miniaturized culturing station that can maintain constant temperature and aeration and culture more than 25 mL and up to 250 mL liquid culture; (d) pH meter equipment converted as an inline sensor of the continuous culturing fluidics; (e) absorbance spectroscopy equipment as an inline sensor of the continuous culturing fluidics. Optical density, measured in a spectrophotometer, can be used as a measure of the concentration of micro-organisms like the bacteria in a suspension. As visible light passes through a cell suspension the light is scattered. Greater scatter indicates that more bacteria or other material is present. The amount of light scatter can be measured in a spectrophotometer. In general, measuring the Optical Density (OD) is a common method to quantify the concentration of substances (Beer-Lambert law), since the light absorbance is proportional to the concentration of the absorbing particles in the sample. The sensors quantify the optical density of a liquid sample by comparing the intensity of light that has passed through and the intensity of the light before it enters the sample. OD also known as "turbidity" taking place at NIR (near-infra red) wavelengths insensitive to changes in media color. All particles that scatter light will be detected, including living and dead micro-organisms as well as micro-organisms debris. Other sensors, such as dissolved oxygen, carbon dioxide, or other metabolites can be included in some embodiments. In some embodiments, the laboratory stations can be modularly provided to expand the functionality of the personal laboratory apparatus.

The application also discloses a kit that includes the personal laboratory apparatus and a wetware kit that includes laboratory supplies (e.g., test tubes, petri dishes, etc.) and a pre-measured volume or mass of ingredients/supplies for performing a laboratory experiment.

Figure 1A:
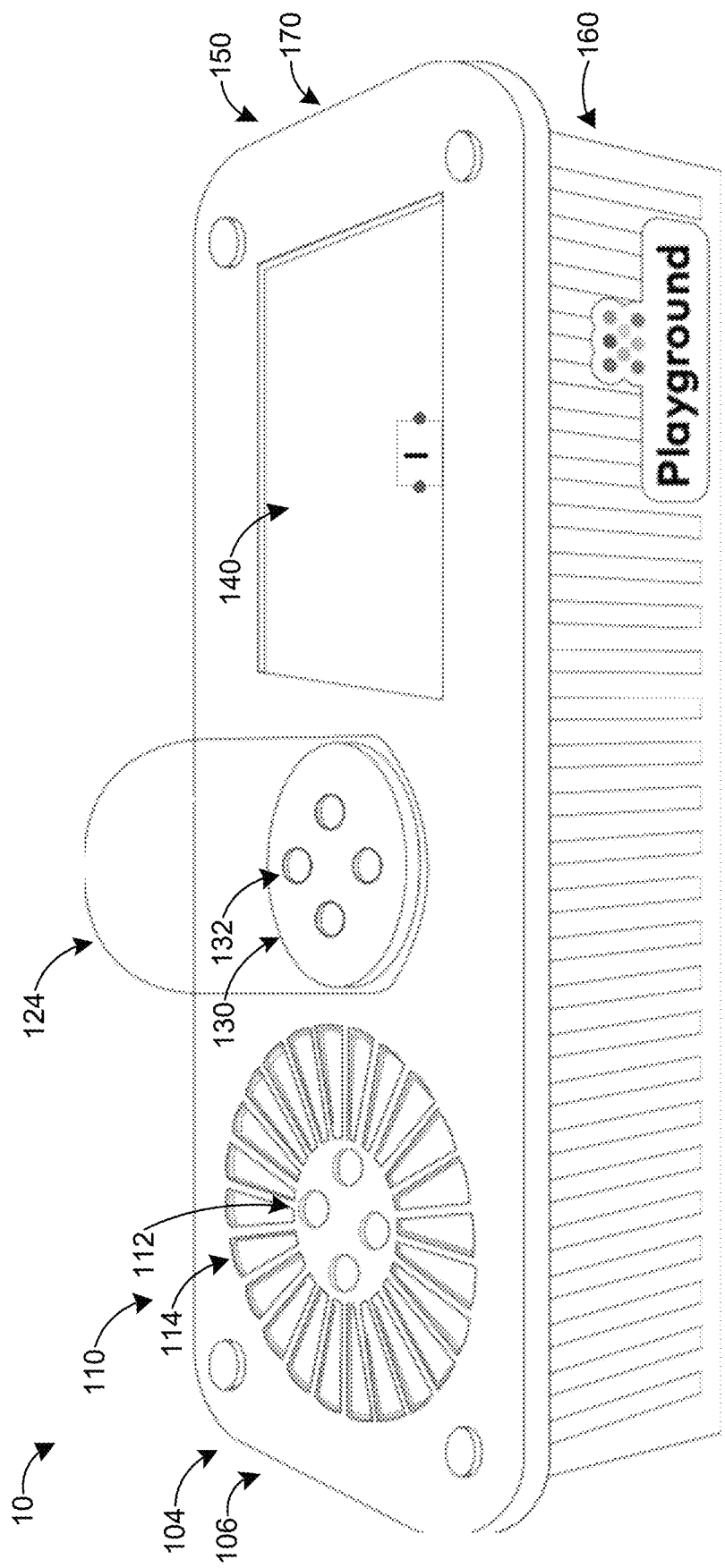
FIG. 1A is a perspective view of a personal laboratory apparatus according to one or more embodiments.

FIG. 1A is a perspective view of a personal laboratory apparatus 10 according to one or more embodiments. The apparatus 10 includes a housing 104 including a cover 106. A plurality of miniaturized laboratory equipment is disposed on and/or in the housing 104, including a tube cooling station 110, an incubator station 120, and a tube heater station 130.

The tube cooling station 110 includes test tube holders 112 to receive test tubes for incubation at a reduced temperature (i.e., below room temperature), which can be maintained through feedback control. The reduced temperature can be about 0° C. to about 17° C., including about 5° C., about 10° C., about 15° C., and any temperature or temperature range between any two of the foregoing temperatures. In one example, the tube cooling station 110 can be set to about 0° C. to about 4° C. or −1° C. to about 6° C., which generally corresponds to ice temperature (or near ice temperature). In another example, the tube cooling station 110 can be set to about 14° C. to about 16° C., which is a desirable temperature for completing DNA ligations. A plurality of air vents 114 are disposed about the perimeter of the tube cooling station 110 to allow air to flow into tube cooling station 110 where it is cooled and circulated by a fan. The overall shape of the air vents 114 has been optimized for air flow and aesthetics.

Within the housing 104, the cooling station 110 can include a Peltier configuration to refrigerate a thermally conductive cooling block that is designed to hold sample tubes (e.g., that functions as test tube holders 112), while the heat is dissipated on a thermally conductive heat sink with a cooling fan operating at about 35 ft$^3$/min (CFM). A thermocouple can be mounted in the cooling block to monitor the temperature of the block. The functional temperature of the cooling block is below room temperature, with one configuration mimicking ice, whereby the target temperature range is between about 0° C. to about 4° C. or about −1° C. to about 6° C. Another configuration for assisting with DNA ligations is between 14° C. and 17° C. Other configurations may be programmed.

The incubator station 120 can receive a petri dish for incubation at an elevated temperature (i.e., above room temperature), which can be maintained through feedback control. The elevated temperature can be any temperature between about room temperature and about 50° C. In some examples, this temperature can be about 30° C. to about 45° C., including about 35° C., about 40° C., and any temperature or temperature range between any two of the foregoing temperatures. In one example, the incubator station 120 can be set to about 30° C. to about 37° C., which can be used for general incubation of cells. In another example, the incubator station 120 can be set to about 42° C., which can be used for heat shocking cells. In one embodiment, the incubator station 120 includes a cover 124 to increase the air temperature above the incubator station 120 to further heat a petri dish disposed in the incubator station 120.

The tube heater station 130 includes test tube holders 132 to receive test tubes for incubation at an elevated temperature, which can include any of the elevated temperatures described above. The test tube holders 132 extend into the housing 104 where they are in thermal communication with components of the tube heater station 130. The test tube holders 132 are disposed on at least a portion of the incubator station 120.

Within the housing 104, the heating station 120 and the tube heater station 130 can include a common heating element or group of elements that is/are disposed below a thermally conductive heating block that is designed to hold sample tubes (e.g., that functions as test tube holders 132) and/or heat a chamber (e.g., incubator station 120) to incubate other samples such as petri dishes, above room temperature. For example, the heating element(s) can be situated between the thermally conductive heating block and a thermally conductive heat sink for enhanced temperature control. A thermocouple or thermistor can be mounted on or embedded within the system so the temperature of the thermally conductive heating block can be obtained and controlled (e.g., via a microcontroller). The functional temperature of the heating block is above room temperature, with one temperature setting mimicking the temperature of the human body in the temperature range of about 36° C. to about 38° C. Another temperature setting can be used to heat shock cells, whereby the target temperature range is about 40° C. to about 43° C. Other temperature settings may be programmed. In one example, a temperature range of 42° C. to 50° C. can be programmed to induce gene expression of temperature sensitive genes.

Various electrical components including a microcontroller, memory, a power converter, a wireless modem and/or Bluetooth and/or a radio (e.g., a cellular radio), and one or more circuit boards are disposed in the housing 104. The microcontroller is in electrical communication with the miniaturized laboratory equipment to provide control signals thereto and to receive data therefrom. For example, the microcontroller provides control signals to the cooling station 110 to set its power or voltage so that the cooling station 110 reduces its temperature to a given reduced temperature set point. In addition, the microcontroller receives data from a thermocouple and/or a thermistor, which provide(s) an output signal corresponding to the temperature in the cooling station 110. The microcontroller can use this data as feedback to adjust the control signals to raise or lower the temperature of the cooling station 110 as appropriate. The same or similar arrangement is provided between the microcontroller and the incubator station 120 and provided between the microcontroller and the tube heater station 130.

The microcontroller aggregates data from the various station sensors, and sends data to a designated server that may be on a public or private network. The server stores, analyses, processes, and/or repurposes the data. The data can be presented back to the user via a web browser or via a native application. The server may also communicate back to the microcontroller or relay information to another compatible device to cause an effect. Multiple multi-use devices may be used to automate various tasks and, with instruction from the server, may or may not autonomously complete the tasks. Access to information about the apparatus 10 performance while the user is not physically co-located with the apparatus 10 can increases user engagement with the apparatus 10.

A touch screen 140 is disposed on the housing 104 to receive user input (e.g., the temperature set points) to control stations 110, 120, and 130, as well as to display the measured temperature of each station 110, 120, and 130. The touch screen 140 is electrically coupled to the microcontroller to send the temperature set points thereto, and to receive signals indicating the measured temperatures therefrom.

Wi-Fi configuration buttons 150 (e.g., to adjust the Wi-Fi configuration settings), a power switch 160, and a power cable inlet 170 are disposed on the housing 104 (e.g., on the side of apparatus 10). The Wi-Fi configuration settings can also be accessed remotely from a separate device, such as a tablet or smartphone, running appropriate software for this purpose. The apparatus 10 includes a network interface to communicate with a wired or a wireless network. Through the network interface, the microcontroller can send and receive data, commands, and/or instructions to/from a central server. A user can remotely access (e.g., via a web application or a native application on the user's computer that is in network communication with the centralized server) the real-time data and/or a modified presentation of the data (e.g., in a graph, in statistical form, etc.) and can control the personal laboratory apparatus 10.

In some embodiments, the apparatus 10 includes an auxiliary electrical control panel whereby the user could connect wires to the apparatus 10 in order to power, control, and/or send/receive data or instructions to/from the auxiliary peripheral unit and laboratory equipment in the apparatus 10. For example, the auxiliary peripheral unit can include protein or nucleic acid gel electrophoresis apparatuses. Desired voltages may range between 1 V and 200 V, and current should not exceed 5 A. In some embodiment, the communication between the auxiliary peripheral unit(s) and the apparatus 10 is done via a Bluetooth or wireless connection or micro-controller.

Figure 1B:
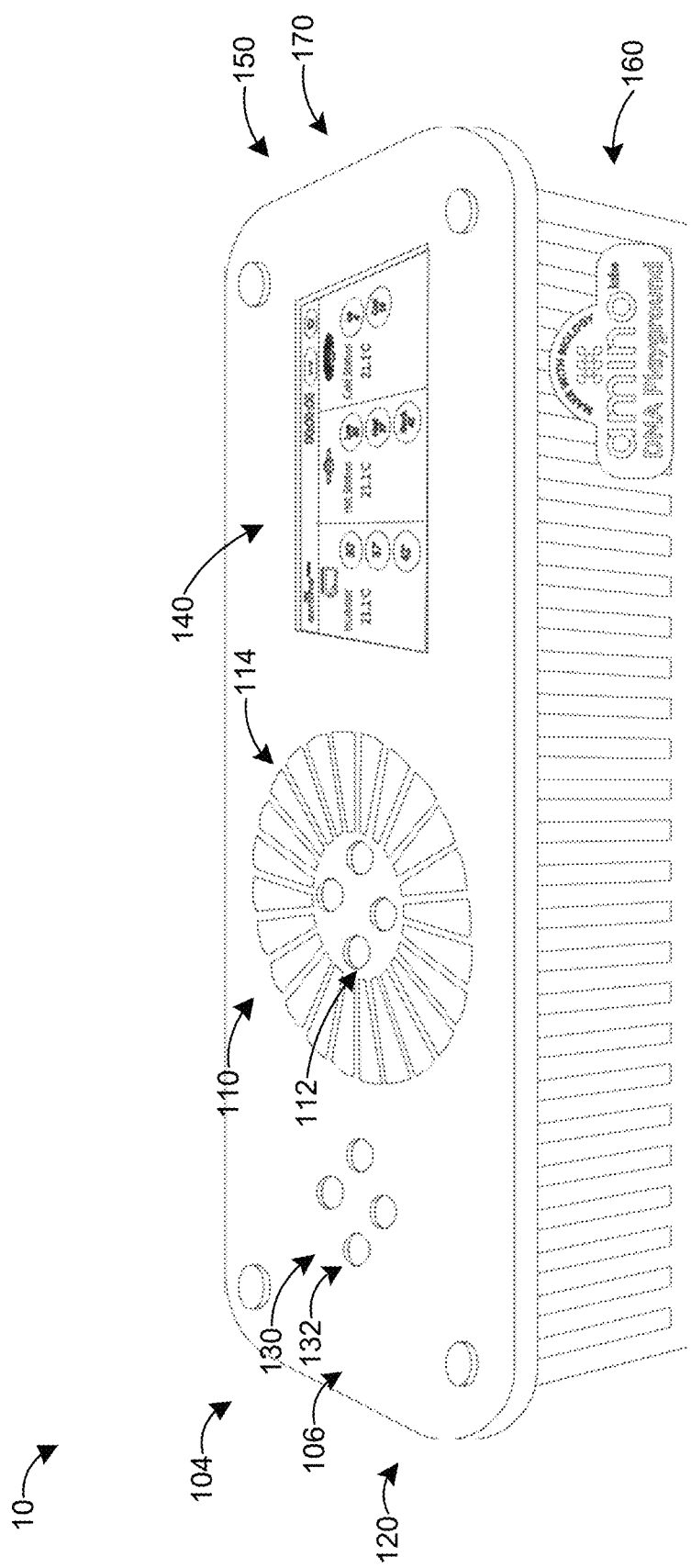
FIG. 1B is a perspective view of a personal laboratory apparatus according to one or more alternative embodiments.

FIG. 1B illustrates personal laboratory apparatus 10 according to one or more alternative embodiments. In FIG. 1B, the incubator station 120 and the tube heater station 130 share a common heating element. The incubator station 120 is disposed in the housing 104 and can be accessed by a door one the side of the housing 104, for example as illustrated in FIG. 10.

Figure 2A:
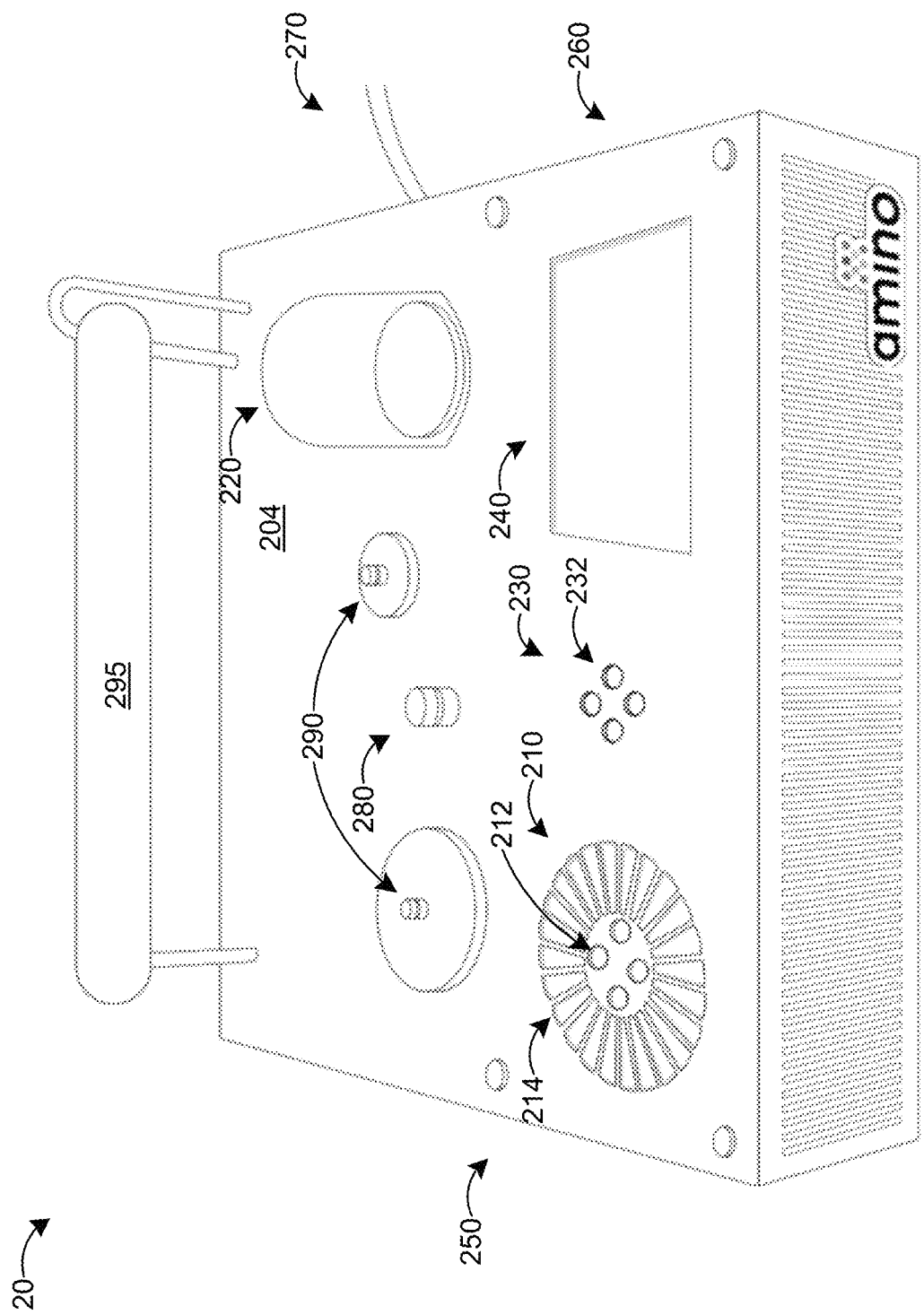
FIG. 2A is a perspective view of a personal laboratory apparatus according to one or more embodiments.

FIG. 2A is a perspective view of a personal laboratory apparatus 20 according to one or more embodiments. The apparatus 20 includes a housing 204. A plurality of miniaturized laboratory equipment is disposed on and/or in the housing 204, including a cooling station 210, an incubator station 220, a tube heater station 230, a touch screen 240, Wi-Fi configuration buttons 250, a power switch 260, a power cable inlet 270, an inoculation port 280, input ports 290, and a bioreactor 295. The cooling station 210, incubator station 220, tube heater station 230, touch screen 240, Wi-Fi configuration buttons 250, power switch 260, and power cable inlet 270 can be the same as or similar to the cooling station 110, incubator station 120, tube heater station 130, touch screen 140, Wi-Fi configuration buttons 150, power switch 160, and power cable inlet 170, respectively. However, it is noted that the test tube holders 232 of the tube heater station 230 are not disposed on at least a portion of the incubator station 220 in apparatus 20. The incubator station 220 and the tube heater station 230 do not share a common heating element as they do in incubator station 120 and tube heater station 130.

The inoculation port 270 can be used to add microorganisms (e.g., via injection) into the fluid network for the bioreactor 295. One or more optional input ports 280 can be used to add foreign substances (e.g., via injection), such as, but not limited to, sugars, buffers, nutrients, inducers and culture modifiers, into the fluid network for the bioreactor 295.

The bioreactor 295 is mounted above the top surface of the housing 204, visible to the user as to increase user engagement. The bioreactor is the primary storage vessel for liquid culture, and in different embodiments the bioreactor may or may not be visually accessible to the user. Increased user engagement and perceived activity occurs when the primary storage vessel and the contents within are visible. The fluid network for the bioreactor, including one or more pumps, pinch valves, check valves, tubes, and sensors, is located in a contained compartment inside the housing 204. The bioreactor 295 is fluidly coupled to the fluid network via tube 291. In some embodiments, some or all of the fluid network can be disposed in a fluid cartridge, which can be replaced as needed. Organisms can be continuously cultured in the bioreactor 295 and the associated fluid network as well as in a petri dish incubator. In some embodiments, more than one bioreactor 285 vessel is available for culturing simultaneously to the user, all or some of which may or may not be visible to the user.

In some embodiments, one or more lights (e.g., LEDs) are disposed in the bioreactor 295 and/or in the fluid network for the bioreactor 295. The lights can provide a narrow or a full spectrum of light energy to illuminate the bioreactor 295, or petri dish incubator, and/or the fluid network for increased user engagement, for aesthetic purposes, for viewing fluorescence or other characteristics of the experiment, or for functional purposes such as to modulate gene expression of genetically-engineered or natural biological systems.

In some embodiments, the apparatus 20 includes two or more bioreactors 295 where each bioreactor 285 has an independent fluid network.

As with apparatus 10, apparatus 20 includes a microcontroller that is in electrical communication with the miniaturized laboratory equipment to provide control signals thereto and to receive data therefrom. The microcontroller can aggregate data from the various station sensors (e.g., as described above), and send data to a designated server that may be on a public or private network. The server stores, analyses, processes, and/or repurposes the data. The data can be presented back to the user via a web browser or via a native application. The server may also communicate back to the microcontroller or relay information to another compatible device to cause an effect. Multiple multi-use devices may be used to automate various tasks and, with instruction from the server, may or may not autonomously complete the tasks. Access to information about the apparatus 20 performance while the user is not physically co-located with the apparatus 20 can increases user engagement with the apparatus 20.

Figure 2B:
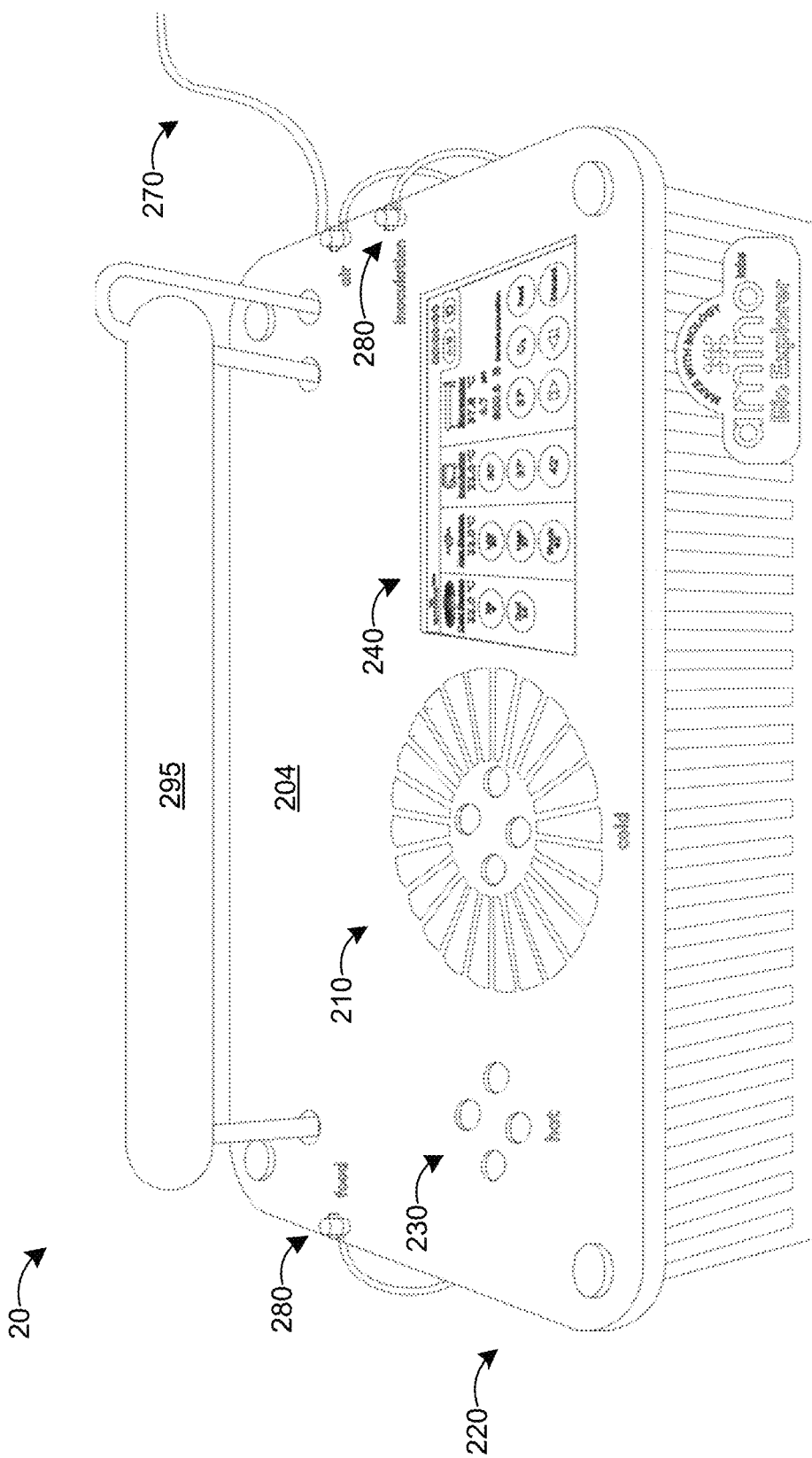
FIG. 2B is a perspective view of a personal laboratory apparatus according to one or more alternative embodiments.

FIG. 2B illustrates personal laboratory apparatus 20 according to one or more alternative embodiments. In FIG. 2B, the incubator station 220 and the tube heater station 230 share a common heating element. The incubator station 220 is disposed in the housing 204 and can be accessed by a door one the side of the housing 204, for example as illustrated in FIG. 10.

FIG. 3A is a top view of a test tube holder 30 according to one or more embodiments. The test tube holder 30 can be the same as or similar to test tube holders 112, 132, 212, and/or 222. The test tub holder 30 comprises an aluminum thermally conductive block 300 in which cavities 310 have been defined (e.g., milled). The dimensions of the cavities 310 correspond to the dimensions of test tube 40, which can be provided with or separately from the apparatus 10, 20. The diameter D1 at the top of the cavity 310 is equal to or slightly greater than the corresponding diameter D2 at a height H2 of the test tube 40 (i.e., just before the diameter of the test tube 40 tapers inwardly). In some embodiments, the dimensions of the cavities 310 correspond to multiple, or different known test tubes including test tube 40. In some embodiments, adapters for cavities 310 to be compatible with common and/or known test tubes in the industry outside can be provided or installed.

Figure 3B:
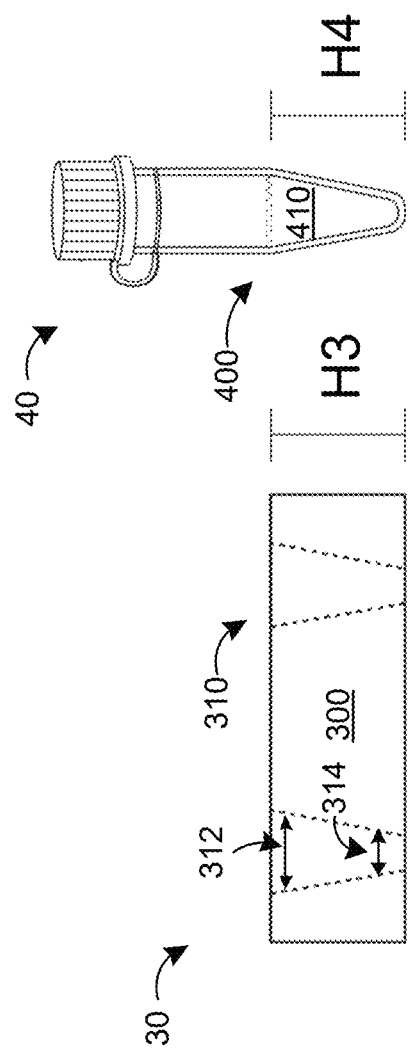
FIG. 3B is a cross-sectional view of the test tuber holder illustrated in FIG. 3A.

FIG. 3B is a cross-sectional view of test tuber holder 30 through line 4-4 in FIG. 3A. As can be seen each cavity 310 tapers from a relatively wide cross-sectional width 312 at the top of the cavity 310 to a relatively narrow cross-sectional width 314 at the bottom of the cavity 310 along its height H3, which corresponds to the dimensions of tapered tip 400 of test tube 40. The matching of the tapering promotes thermal contact and thermal transfer between the test tube 40 and the thermal block 300.

When the test tube holder 30 is the same as the test tube holders 112, 212 in the cooling station 110, 210, the height H3 of the cavities 310 should be greater than or equal to about 1.1 times the marked height H4 of liquid 410 in test tube 40 to achieve the desired cooled temperature of the liquid 410. When the test tube holder 30 is the same as the test tube holders 132, 232 in the tube heater station 130, 230, the marked height H4 of liquid 410 in test tube 40 can be less than or equal to about 3 times the height H3 of the cavities 310 to achieve the desired heated temperature of the liquid 410 at room temperature. In some embodiments, the marked height H4 of liquid 410 in test tube 40 can be less than or equal to about 3 times the height H3, including less than or equal to about 2.5 times the height H3, less than or equal to about 2 times the height H3, less than or equal to about 1.5 times the height H3, and less than or equal to about 1 times the height H3, including any heights or height ranges between any two of the foregoing heights.

Figure 4:
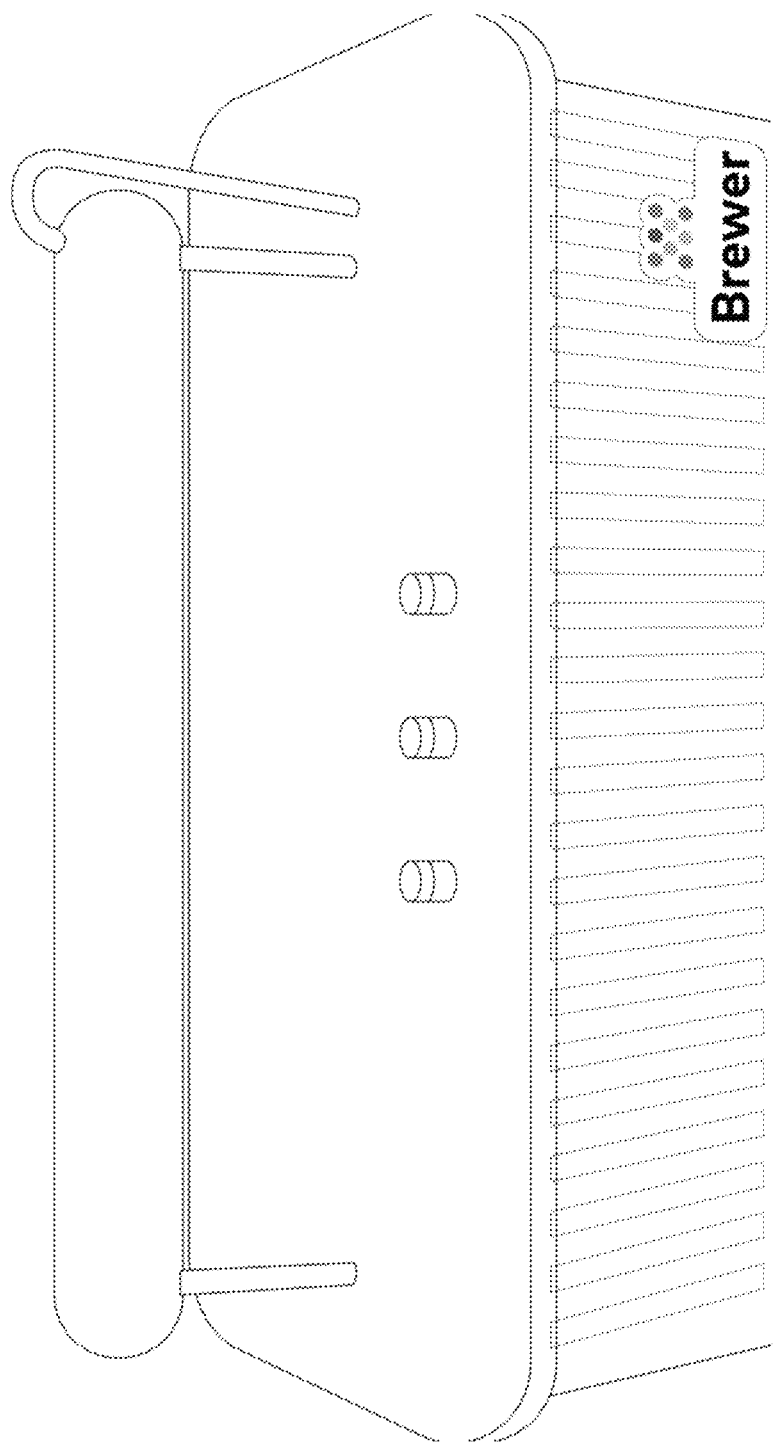
FIG. 4 is an exemplary perspective view of a brewer apparatus.

FIG. 4 is a perspective view of a brewer apparatus 4000 according to one or more embodiments. The brewer apparatus 4000 includes a bioreactor 4095 and an associated fluid network, which can be the same as bioreactor 295 and its fluid network. The brewer apparatus 4000 also include input ports 4100, which can be the same as inoculation port 270 and/or input ports 280. The brewer apparatus 4000 can be fluidly connected to a personal laboratory apparatus (e.g., personal laboratory apparatus 10, 20) to modularly expand it. In the case of personal laboratory apparatus 20, connecting brewer apparatus 4000 to laboratory apparatus 20 allows the user to operate two bioreactors (e.g., bioreactors 295, 4095) from the same controls including using touch screen 240. Alternatively, brewer apparatus 4000 can be operated independently.

Figure 5:
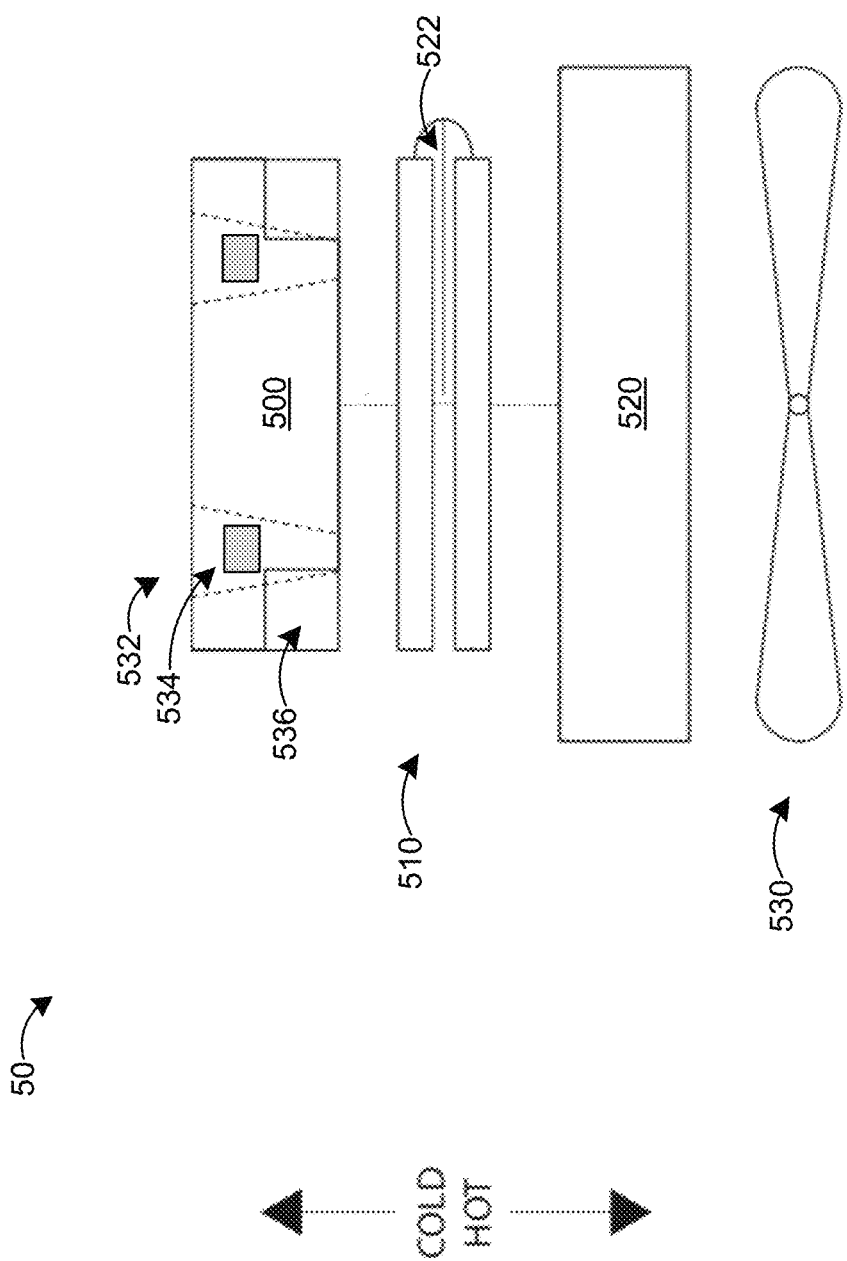
FIG. 5 is a side view of a cooling station according to one or more embodiments.

FIG. 5 is a side view of a cooling station 50 according to one or more embodiments. Cooling station 50 can be the same as, similar to, or different than cooling stations 110, 210, described above. Cooling station 50 includes a thermally conductive test tube holder 500, thermoelectric devices 510, a heat sink 520, and a fan 530. The thermally conductive test tube 500 holder includes a thermally conductive block (e.g., a metallic block such as an aluminum block) having cavities 532 defined therein. Each cavity 532 is sized to conform to at least a portion of a test tube. In some embodiments, the thermally conductive test tube holder 500 is the same as or similar to test tube holder 30, described above. A thermistor 534 (or other temperature-sensitive component such as a thermocouple) is disposed on an internal wall of the cavities 532 and/or in the thermally conductive block to monitor the temperature of the thermally conductive test tube holder 500, which can be used as feedback for the microcontroller to adjust control signals to raise or lower the power to thermoelectric devices 510 to provide more or less cooling energy. The test tube holder 500 also includes notches 536 that fit into a corresponding fiberglass holder on the apparatus (e.g., apparatus 10, 20) to align the test tube holder 500 in place on top of the thermoelectric devices 510.

The thermoelectric devices 510 may be electrically connected in series or in parallel to each other and may be fixed together using a thermoelectric paste 522. The thermoelectric devices 510 can operate at about 30 W of power or more in some embodiments. The thermoelectric devices 510 include two or more solid-state devices that operate according to the Peltier effect to provide precise temperature control. The Peltier effect creates a temperature difference by transferring heat between two electrical junctions supplied by DC current. The cooling effect is proportional to the number of coolers used. In some embodiments, multiple thermoelectric coolers (e.g., solid-state devices) are connected and then placed between two metal plates. The thermoelectric devices 510 are in thermal communication with the thermally conductive test tube holder 500 to provide thermal energy thereto. For example, the thermoelectric devices 510 can reduce or increase the temperature of the thermally conductive test tube holder 500 according to control signals received from the microcontroller (and feedback from the thermistor 534).

The heat sink 520 is disposed below the thermoelectric devices 510 on their "hot" side. The heat sink 520 is a thermally conductive body (e.g., a metal) configured to thermally conduct heat away from the thermoelectric devices 510 and towards the fan 530, which can provide about 35 cubic feet per minute (CFM) or more of air flow to improve thermal transfer (e.g., due to convection) from the heat sink 520 to the surrounding environment. In some embodiments, the heat sink of 520 is an aluminum disk with or without a copper core. The airflow is as follows: air comes in through the air vents (e.g., air vents 114) in the personal laboratory, located around the tube holders. The air then passes over the heat sink 520 where thermal energy is transferred to the air. The heated air then flows out through vents on the front and/or bottom of the personal laboratory. The personal laboratory is also raised from the table surface by 4 support "feet" to promote the air flow. In some embodiments, the heat sink 520 and fan 530 are provided as a single unit, such as the D60188-001 Heat Sink/Cooling Fan Assembly, available from Circuit Specialists of Tempe, Ariz.

Figure 6:
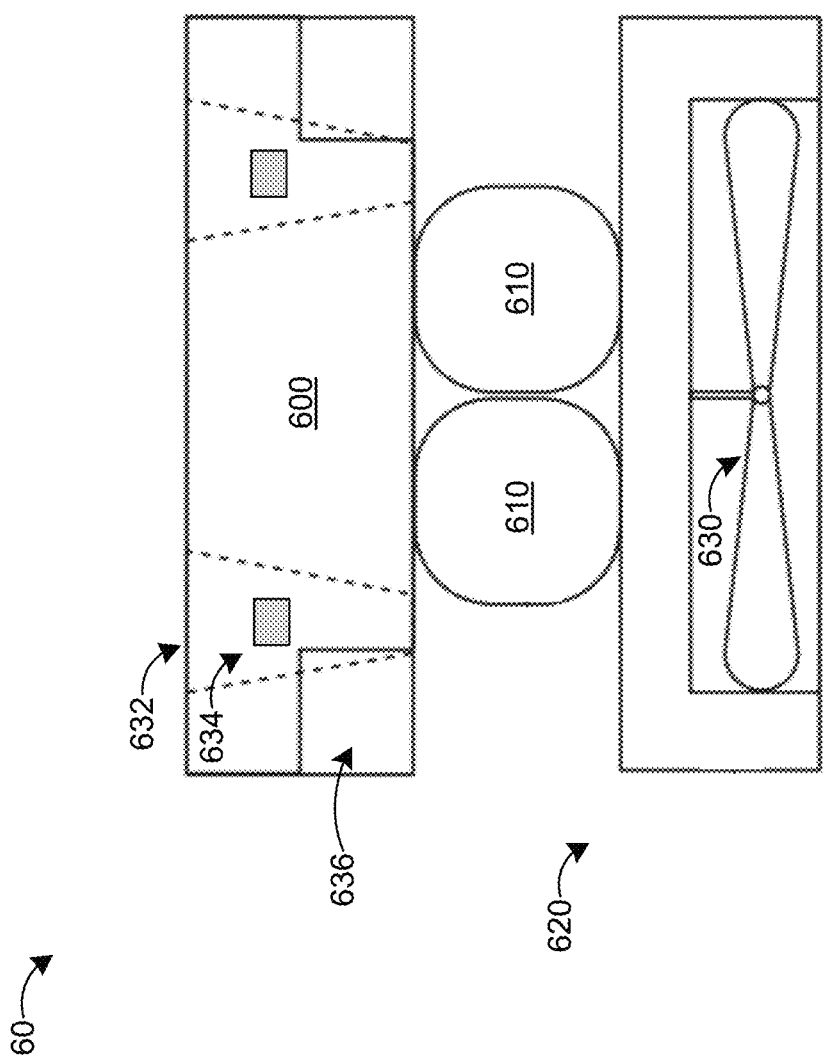
FIG. 6 is a side view of a tube heater station according to one or more embodiments.

FIG. 6 is a side view of a tube heater station 60 according to one or more embodiments. Tube heater station 60 can be the same as, similar to, or different than tube heater stations 130, 230, described above. Tube heater station 60 includes a thermally conductive test tube holder 600, resistive heating elements 610, an optional heat sink 620, and an optional fan 630. The thermally conductive test tube holder 600 includes a thermally conductive block (e.g., a metallic block such as an aluminum block) having cavities 632 defined therein. Each cavity 632 is sized to conform to at least a portion of a test tube. In some embodiments, the thermally conductive test tube holder 600 is the same as or similar to test tube holder 30, described above. A thermistor 634 (or other temperature-sensitive component such as a thermocouple) is disposed on an internal wall of the cavities 632 and/or in the thermally conductive block to monitor the temperature of the thermally conductive test tube holder 600, which can be used as feedback for the microcontroller to adjust control signals to raise or lower the power to resistive heating elements 610 to provide more or less heating energy. Peltiers can be used for this purpose in some exemplary cases. The thermally conductive test tube holder 600 also includes notches 636 that fit into a corresponding plastic holder on the apparatus (e.g., apparatus 10, 20) to align the thermally conductive test tube holder 600 in place on top of the resistive heating elements 610.

The resistive heating elements 610 are disposed below and in direct physical contact with the thermally conductive test tube holder 600 and with the optional heat sink 620. The resistive heating elements 610 can operate at about 40 W of power or less in some embodiments. Optionally, a single station can be used to heat and/or cool as needed using peltiers. In some embodiments, the resistive heating elements 610 are aluminum wire wound resistors capable of dissipating high power in a limited space with relatively low surface temperature. The power is rapidly dissipated as heat through the aluminum housing to a specified heatsink. Two wire-wound chassis mount Resistors are soldered in parallel. The resistive heating elements 610 are in thermal communication with the thermally conductive test tube holder 600 to provide thermal energy thereto. For example, the resistive heating elements 610 can reduce or increase the temperature of the thermally conductive test tube holder 600 according to control signals received from the microcontroller (and feedback from the thermistor 634). In an alternative embodiment, the resistive heating elements 610 can include two or more solid-state devices that operate according to the Peltier effect, such as thermoelectric devices 510.

The optional heat sink 620 is disposed below and in direct physical contact with the resistive heating elements 610 on their "hot" side. The optional heat sink 620 is a thermally conductive body configured to thermally conduct heat away from the resistive heating elements 610 (e.g., to prevent overheating) and towards the optional fan 630, which can provide about 5 to 10 CFM or more of air flow to improve thermal transfer (e.g., due to convection) from the optional heat sink 620 to the surrounding environment. The heat sink 620 can include an aluminum block coupled to the fan 630, which can be the same as heat sink 520 and fan 530, respectively.

The airflow requirements are modest (e.g., 5 to 12 CFM) with the high efficiency of resistive heating elements 610, is as follows: room-temperature air enters from the top, around the test tube holder 600, while warmed air exits at the bottom of the heatsink 620 due to the rotation of the fan 630. The fan 630 channels the warmed air into the incubator chamber (e.g., incubator chamber 740), while also circulating the warmed air inside the incubator chamber.

Figure 7:
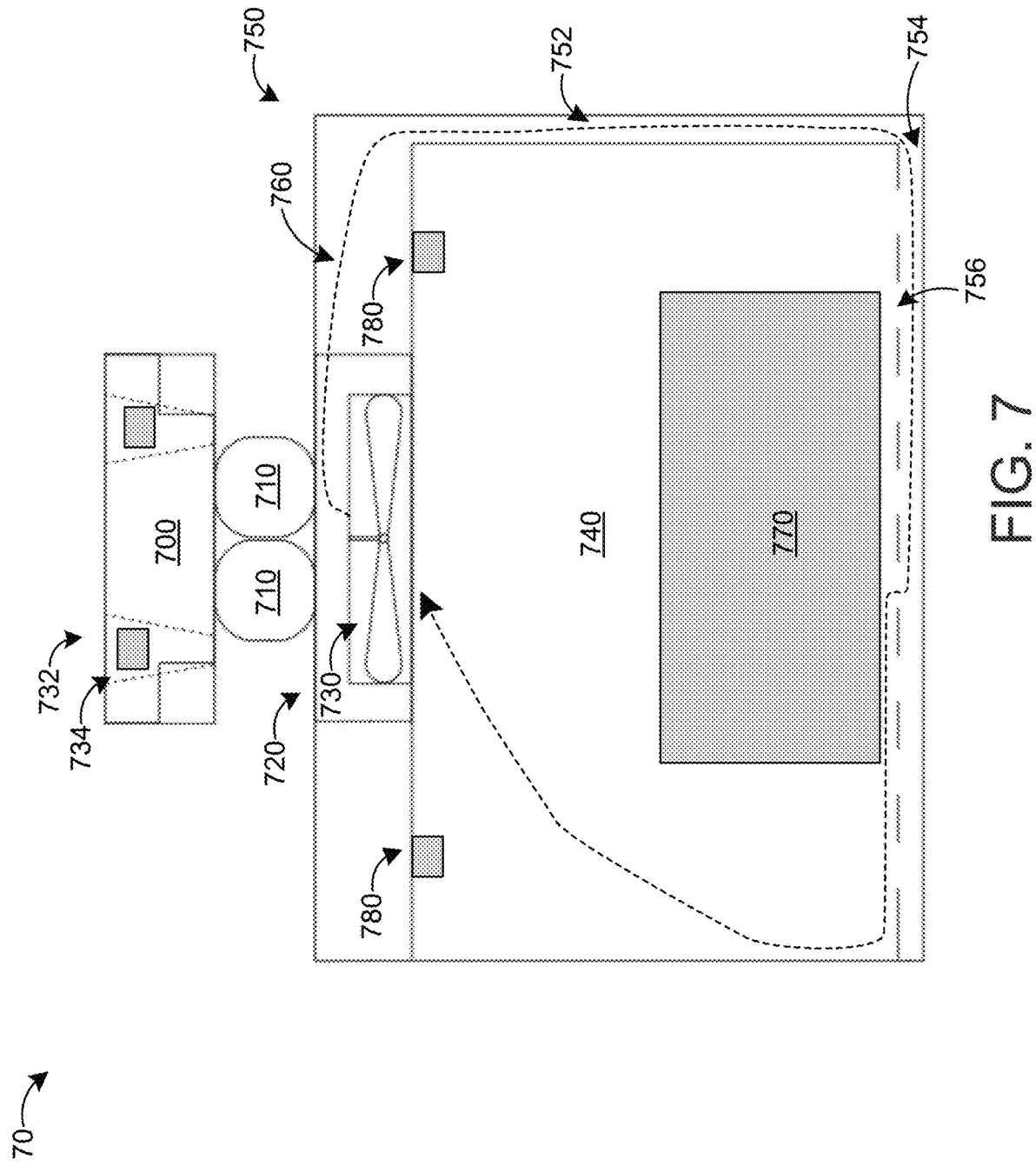
FIG. 7 is a side view of an incubator station according to one or more embodiments.

FIG. 7 is a side view of an incubator station 70 according to one or more embodiments. Incubator station 70 can be the same as, similar to, or different than incubator stations 120, 220, described above. Incubator station 60 includes an optional thermally conductive test tube holder 700, resistive heating elements 710, a heat sink 720, a fan 730, and an incubator chamber 740. The optional thermally conductive test tube holder 700 includes a thermally conductive block (e.g., a metallic block such as an aluminum block) having cavities 732 defined therein. Each cavity 732 is sized to conform to at least a portion of a test tube. In some embodiments, the optional thermally conductive test tube holder 700 is the same as or similar to test tube holder 30 and/or test tube holder 600, described above. A thermistor 734 (or other temperature-sensitive component such as a thermocouple) is disposed on an internal wall of the cavities 732 and/or in the thermally conductive block to monitor the temperature of the optional thermally conductive test tube holder 700, which can be used as feedback for the microcontroller to adjust control signals to raise or lower the power to resistive heating elements 710 to provide more or less heating energy.

The resistive heating elements 710 are disposed below and in direct physical contact with the optional thermally conductive test tube holder 700 and with the heat sink 720. The resistive heating elements 710 can operate at about 40 W of power or less in some embodiments. The resistive heating elements 710 are in thermal communication with the optional thermally conductive test tube holder 700 to provide thermal energy thereto. For example, the resistive heating elements 710 can reduce or increase the temperature of the optional thermally conductive test tube holder 700 according to control signals received from the microcontroller (and feedback from the thermistor 734).

The heat sink 720 is disposed below and in direct physical contact with the resistive heating elements 710. The heat sink 720 is a thermally conductive body configured to thermally conduct heat away from the resistive heating elements 710 towards the fan 730, which can provide about 35 CFM or more of air flow. The heat sink 720 and the fan 730 are enclosed in a heating chamber 750. In operation, the fan 730 draws air 760 from the heating chamber 750 and forces it down a side channel 752. The air 760 is heated by the heat sink 720 before it flows down the side channel 752. The heated air 760 then flows from the side channel 752 into a floor channel 754 disposed below the incubator chamber 740. The top of the floor channel 754 (and the floor of the incubator chamber 740) includes slits 756 that allow the heated air 760 to flow into the incubator chamber 740.

The incubator chamber 740 is sized to accept a petri dish 770, which can be placed on the floor of the incubator chamber. For example, the incubator chamber 740 can be sized (i.e., having a width and a depth) to accept a 60 mm petri dish having a maximum diameter of 67 mm. In another example, the incubator chamber incubator chamber 740 can be sized (i.e., having a width and a depth) to accept a 35 mm petri dish, a 60 mm petri dish, and/or a 100 mm petri dish. In yet other embodiments, four petri dishes may be configured in two double stacks of 60 mm petri dishes disposed side by side.

When the petri dish 770 is placed on the floor of the incubator chamber 740, the heated air 760 flows across the back of the petri dish 770 before rising up to the fan 730 where the air 760 is recirculated through the heating chamber 750. The fan 730 is disposed on the top of the incubator chamber 740 in a fan-sized cutout, such that the fan 730 is exposed to the incubator chamber 740 and the air therein.

The microcontroller can receive a signal from a thermocouple or thermistor disposed in the incubator chamber 740 and/or in the floor channel 754, which the microcontroller can use as feedback to control the power to the resistive elements 710 and/or the speed of the fan 730. The microcontroller can output corresponding control signals to the resistive elements 710 and/or the fan 730 based on the signal from the thermocouple or thermistor. For example, if the signal from the thermocouple or thermistor indicates that the measured temperature is below the temperature set point, the microcontroller can generate control signals that cause the resistive elements 710 to consumer more power and/or to cause the fan 730 speed to decrease or increase as necessary. Conversely, if the signal from the thermocouple or thermistor indicates that the measured temperature is above the temperature set point, the microcontroller can generate control signals that cause the resistive elements 710 to consumer less power and/or to cause the fan 730 speed to increase or decrease as necessary.

In some embodiments, one or more lights (e.g., light emitting diodes (LEDs)) 780 are disposed in the incubator chamber 740. The lights 780 can provide a narrow or a full spectrum of light energy to illuminate the petri dish 770 for increased user engagement, for aesthetic purposes, for viewing fluorescence or other characteristics of the experiment, or for functional purposes such as to modulate gene expression of genetically-engineered or natural biological systems.

Incubator station 70 can be integrated into a personal laboratory apparatus (e.g., personal laboratory apparatus 10, 20) or it can be a modular unit to modularly expand the functionality of the personal laboratory apparatus.

Figure 8:
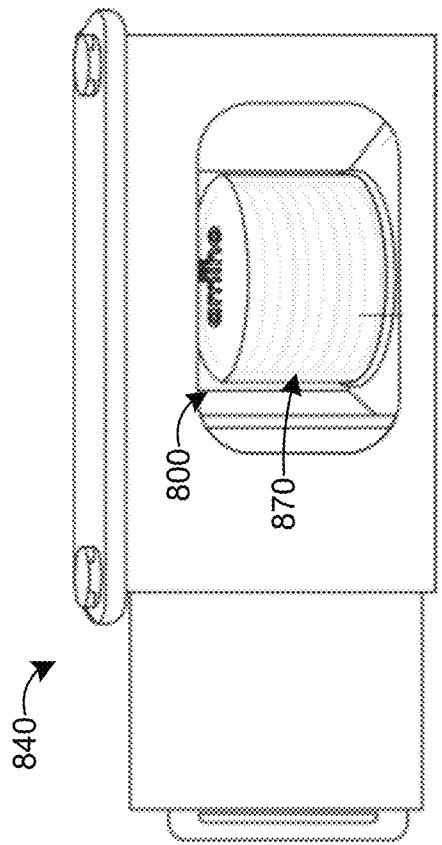
FIG. 8 is a perspective view of a humidity chamber according to one or more embodiments.
Figure 8:
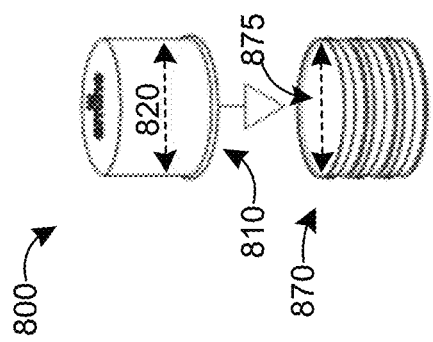

FIG. 8 is a perspective view of a humidity chamber 800 according to one or more embodiments. The humidity chamber 800 is sized to receive a petri dish 870 through an open end 810. For example, the cross-sectional diameter 820 of the humidity chamber 800 is larger or slightly larger than the cross-sectional diameter 875 of the petri dish 870. The humidity chamber 800 generally conforms to the shape and dimensions of the petri dish 870. For example, the humidity chamber 800 is cylindrical to receive and conform to the cylindrical petri dish 870. The humidity chamber 800 is formed of a material that is resistant to air flow and to water vapor to prevent accelerated evaporation and drying out of the agar (e.g., Luria Broth agar) and biological samples. In one example, the humidity chamber 800 is formed of polyethylene terephthalate glycol (PETG). The humidity chamber 800 is sized to fit inside the incubator chamber 840, which can be the same as or similar to incubator chamber 740. The humidity chamber 800 is, in some embodiment, able to accept the insertion of one or more LEDs/lights which can be the same light(s) 780 or from another source.

Figure 9:
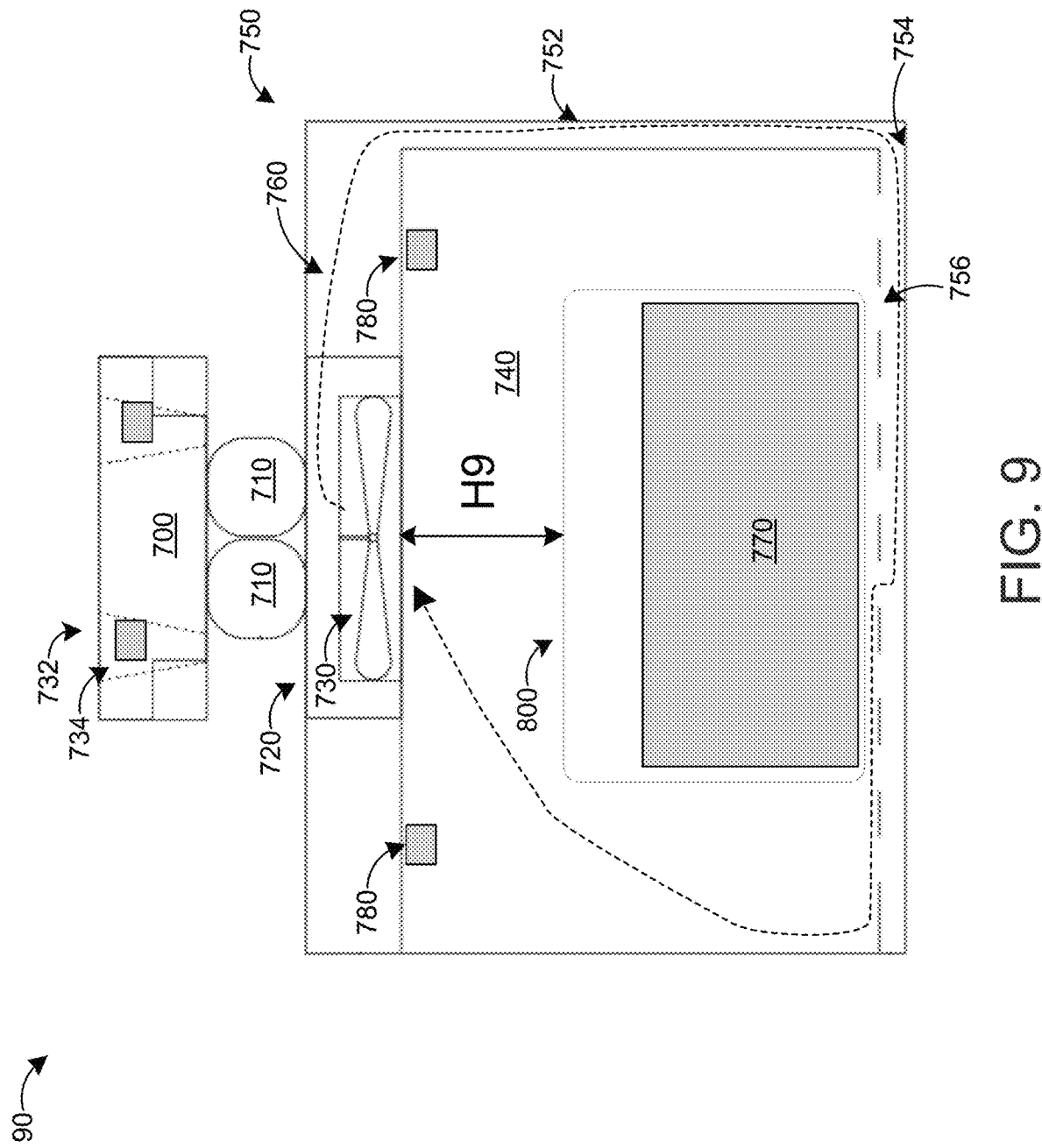
FIG. 9 is side view of an incubator station according to one or more embodiments.

FIG. 9 is side view of an incubator station 90 according to one or more embodiments. Incubator station 90 is the same as or similar to incubator station 70. The incubator chamber 740 is configured so that the main air flow out (e.g., through slits 756) is not blocked or covered by the humidity chamber 800 when it is centered in the incubator chamber 740. The bottom or floor of the incubator chamber 740 can include a raised or lowered feature to center the humidity chamber 800 in the incubator chamber 740. For example, the bottom or floor of the incubator chamber 740 can include a raised or lowered circle that corresponds to the dimensions of the humidity chamber 800. In another example, the bottom or floor of the incubator chamber 740 can include a raised or lowered right triangle in which the humidity chamber 800 can only fit in the centered position. In another embodiment, a raised feature (e.g., a triangle such as a right triangle) is disposed in the back of the incubator chamber 740 and the humidify chamber 800 is in the center position when the humidity chamber 800 is disposed against the raised feature.

The distance H9 between the top of the humidity chamber 800 and the top of the incubator chamber 740 can be less than or equal to about 20 mm to ensure effective airflow and to prevent component pressure loss.

FIG. 10 is a front view 1001 and a perspective view 1002 of an incubator station 1000 according to one or more embodiments. Incubator station 1000 can be the same as or similar to incubator stations 70 and/or 90. In the front view 1001, the door 1010 of the incubator station 1000 is in the open position. The door 1010 can be slid open using door handle 1012. The open position provides access to incubator chamber 1040, for example to place or remove a petri dish or to perform maintenance on the incubator station 1000.

In the perspective view 1002, the door 1010 of the incubator chamber 1040 is slid to the closed position. The door handle 1012 extends beyond the door 1010 to allow a user to grip the door handle 1012 to slide open the door 1010. A door lock 1030 can engage a slot on the inside of the door 1010 to lock the door 1010 closed. Locking the door 1010 can ensure that the door 1010 is fully closed and can prevent any deliberate or unintentional tampering with the petri dish while it is in the incubator chamber 1040. The door 1010 includes an optional window 1014 to allow the user to see into the incubator chamber 1040, which can promote user engagement with the personal laboratory.

The door 1010 can include a small hole 1020 (e.g., a pinhole) for taking photographs of the bacteria in the incubator chamber 1040. The incubator chamber 1040 can function as a light-proof box. Light can enter the small hole 1020 and can be reflected by a mirror disposed on the top or ceiling of the incubator chamber 1040 onto the petri dish, which can be coated with light-reactive bacteria. The pinhole diameter and depth follows the equation $d=2\sqrt{f\lambda}$ where d is the pinhole diameter, f is focal length (distance from pinhole to image plane) and $\lambda$ is the wavelength of light.

Figure 10B:
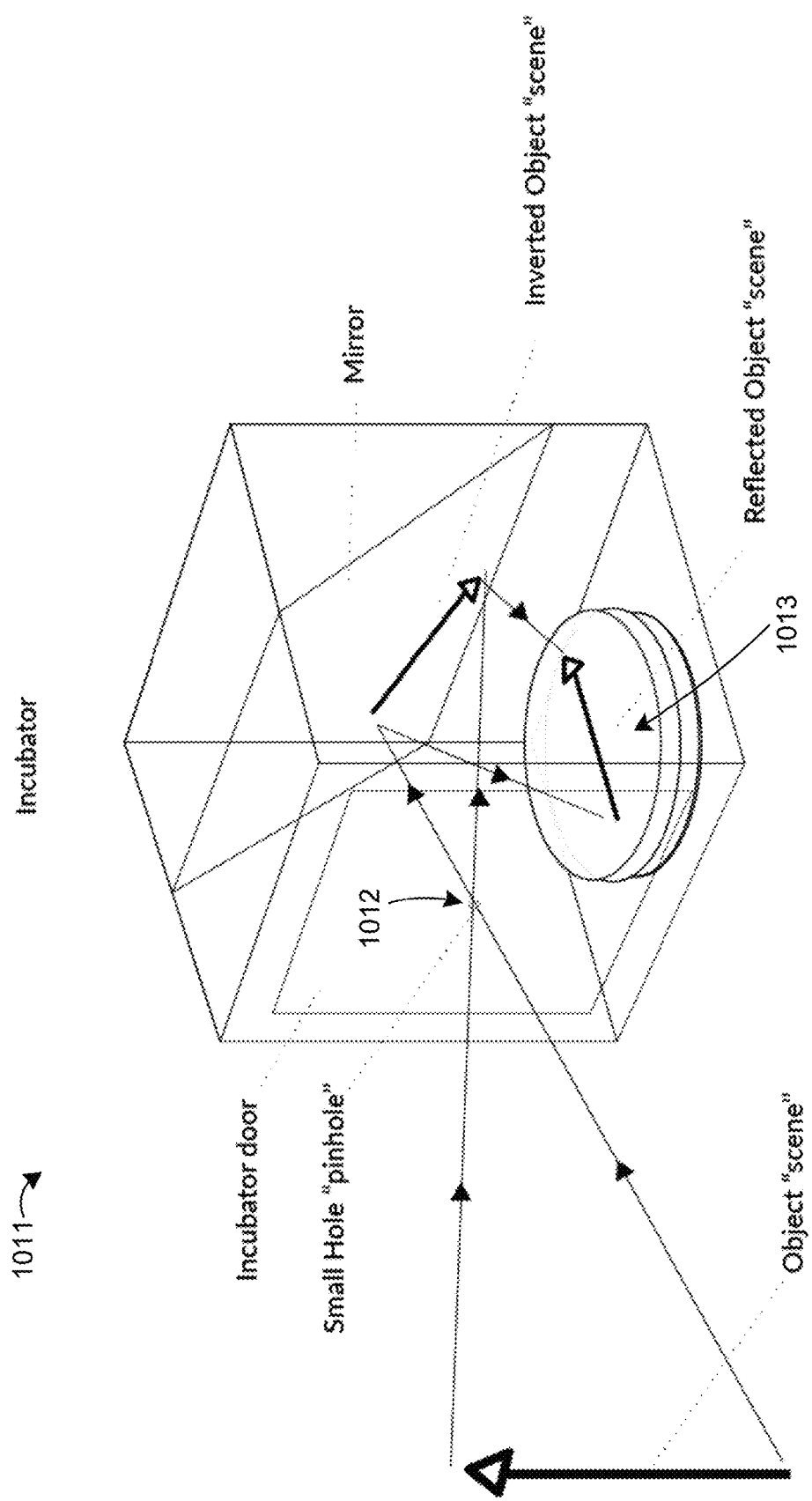
FIG. 10B illustrates a representation of an incubator acting as a camera obscura.

FIG. 10B illustrates a representation of an incubator acting as a camera obscura 1011 including an incubator chamber as discussed before, with a door and a small pinhole therein 1012. Here, the bacteria themselves 1013 will act as the "film" to be exposed. The bacteria change colors to correspond to the wavelength of lights that hits them, similar to a color film in a camera.

Figure 11:
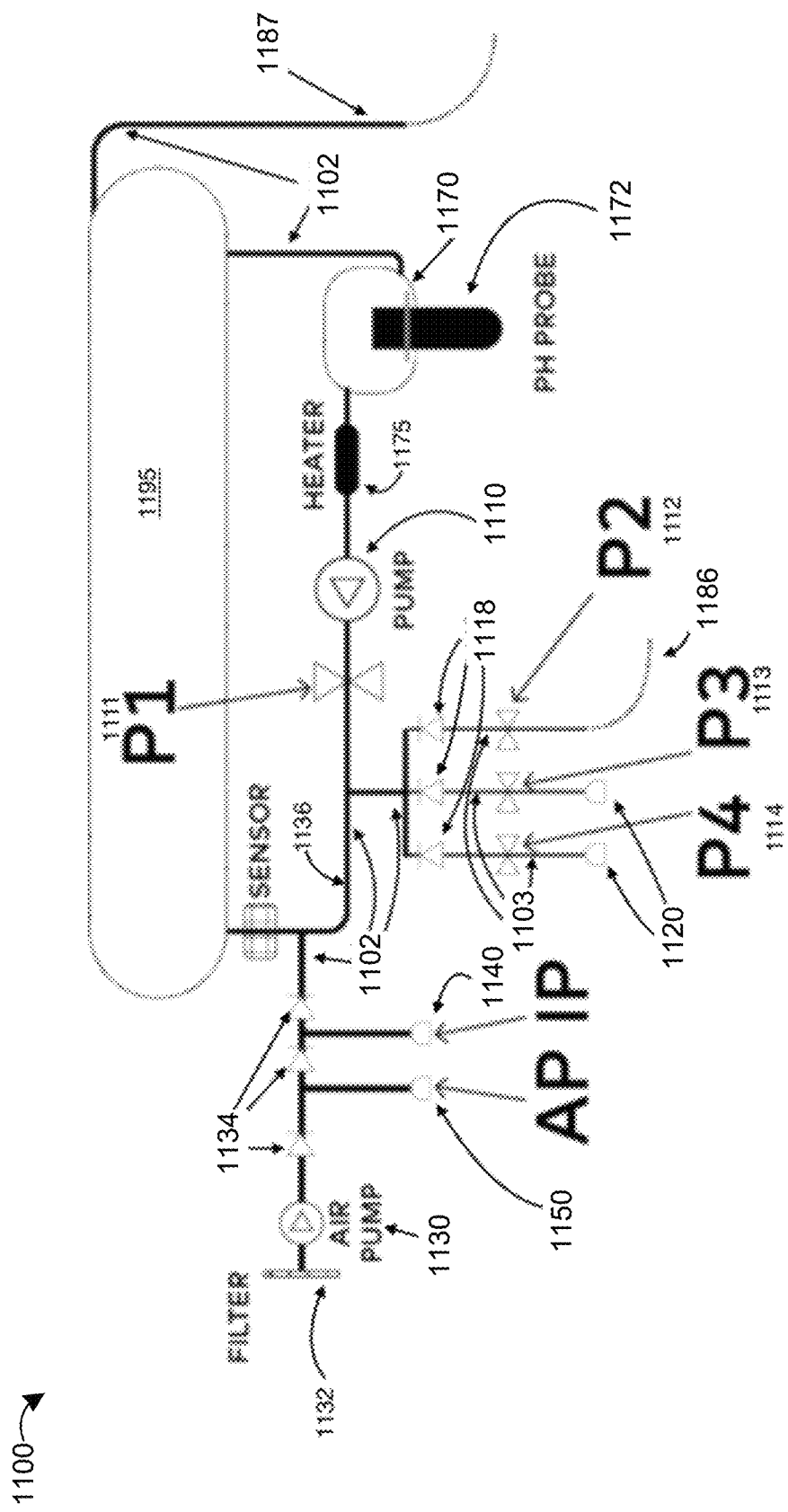
FIG. 11 is a schematic representation of a fluidic "circuit" for a bioreactor according to one or more embodiments.

FIG. 11 is a schematic representation of a fluidic "circuit" 1100 for a bioreactor 1195 according to one or more embodiments. The bioreactor 1195 can be the same as or similar to the bioreactor 295. Thus, the fluid circuit 1100 can be disposed in at least a portion of the housing 204 of the personal laboratory apparatus 20.

The various components of the fluidic circuit 1100 are connected by tubes 1102 and 1104. In some embodiments, tubes 1104 are narrower than tubes 1102; for example, tubes 1104 could have inner and outer diameters of ¹⁄₁₆ inch and ⅛ inch respectively, and tubes 1102 could have inner and outer diameters of ⅛ inch and ¼ inch respectively. A peristaltic pump 1110 drives the flow of liquid in a forward (i.e. leftward/clockwise) or reverse (i.e. rightward/counterclockwise) direction within the system. Forward direction capabilities include disposal of liquid from the system through the disposal line 1186 when the disposal pinch valve 1112 (P2) is open and the main pinch valve 1111 (P1) is closed, and standard circulation of the culturing when P1 is open and P2-P3 (1112-1113) are closed. Reverse direction capabilities include input of liquid via auxiliary port when Aux port pinch valve 1113 (P3) is open and main pinch valve 1111 (P1) is closed. Check valves 1118 on the input Aux port(s) 1120 further ensure unidirectional flow. Aeration includes an air pump 1130 with a microfilter 1132 that pushes air through a series of check valves 1134 and feeds into the main line 1136 after P1. The inoculation port 1140 (IP: where microorganisms are injected into the system), is in line with the air pump 1130 and includes a check valve 1134 to ensure unidirectional flow of liquid into the main line 1136. The airport 1150 (AP) line is used to clean the tubing adjacent to the inoculation port 1140 and feeds into the main line 1136. After P1 and the AP, IP adjoining line, is the input to the main bioreactor 1195. The main bioreactor 1195 has two outputs, one to the sensor chamber 1170, and an overflow which includes a check valve that connects to the disposal line. In addition, the main bioreactor 1195 can vent gases through the air out line 1187. The sensor chamber may contain a pH probe 1172 and/or other sensors. The sensor chamber 1170 feeds into the primary heating element which then connects to the pump 410.

The fluidics components of the device enable the controlled flow of the continuously cultured organisms, as well as enable liquids to be added to the continuous culture, or for the liquid and/or culture to be expelled from the system. A single liquid pump operates in forward or reverse flow of liquid, and pinch valves are used to block or allow flow through certain tubes or pathways. Check valves aid in ensuring that fluid flows in the proper direction. Other configurations may include multiple pumps that can be used to cause fluid motion. In-line sensors that directly interact with the inside fluid or that do not directly interact with the inside fluid are used to analyze the fluids component. Sensors include but are not limited to monitoring pH, temperature, cells count, EMR absorbance, fluorescence or luminescence, oxygen, carbon dioxide, or other metabolites such as but not limited to acids, bases, alcohols, ketones, aldehydes, lipids. The sensors have transducer elements that result in distinguishable electronic configurations that can be read by the device's central processing unit.

In some embodiments, some or all of the fluidics components of the device may be contained in a separate, removable module. The module would allow for simple removal and replacement with another new or refurbished module. Such interchangeable modules could be termed "cassettes," "cartridges," "fluidics chips" or other terms. An integrated fluidics module simplifies the design of the machine by replacing many connectors such as elbows and T-connectors, and allows the user to easily replace or refurbish the fluidics components. Furthermore, a removable fluidics module may replace the external reactor, such as bioreactor 295 in FIG. 2A, allowing for a more compact, robust and mobile design for the machine (e.g., someone could put the machine in their backpack).

Figure 12:
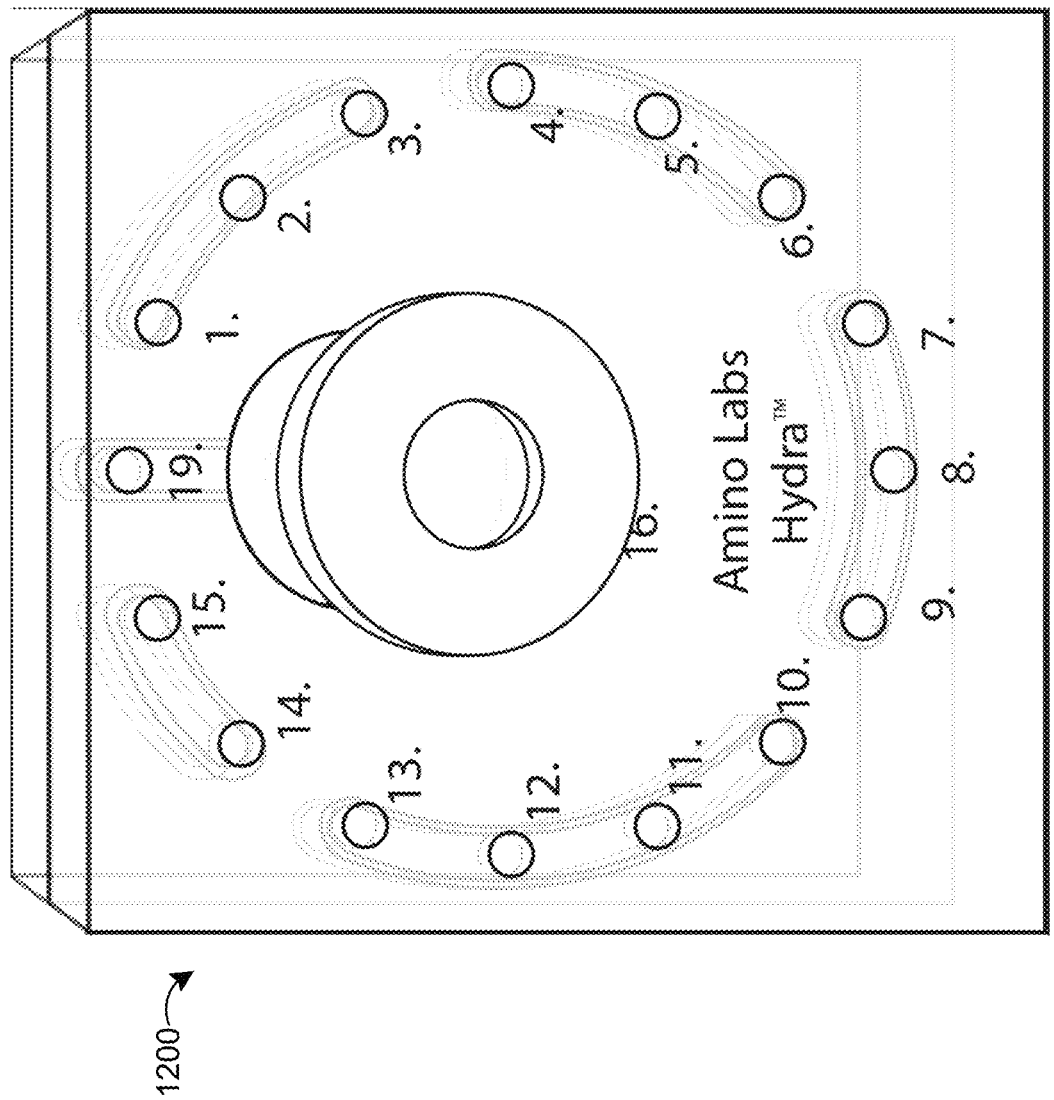
FIGS. 12 and 13 illustrate front and back views, respectively, of a removable fluidics chip according to one or more embodiments.
Figure 13:
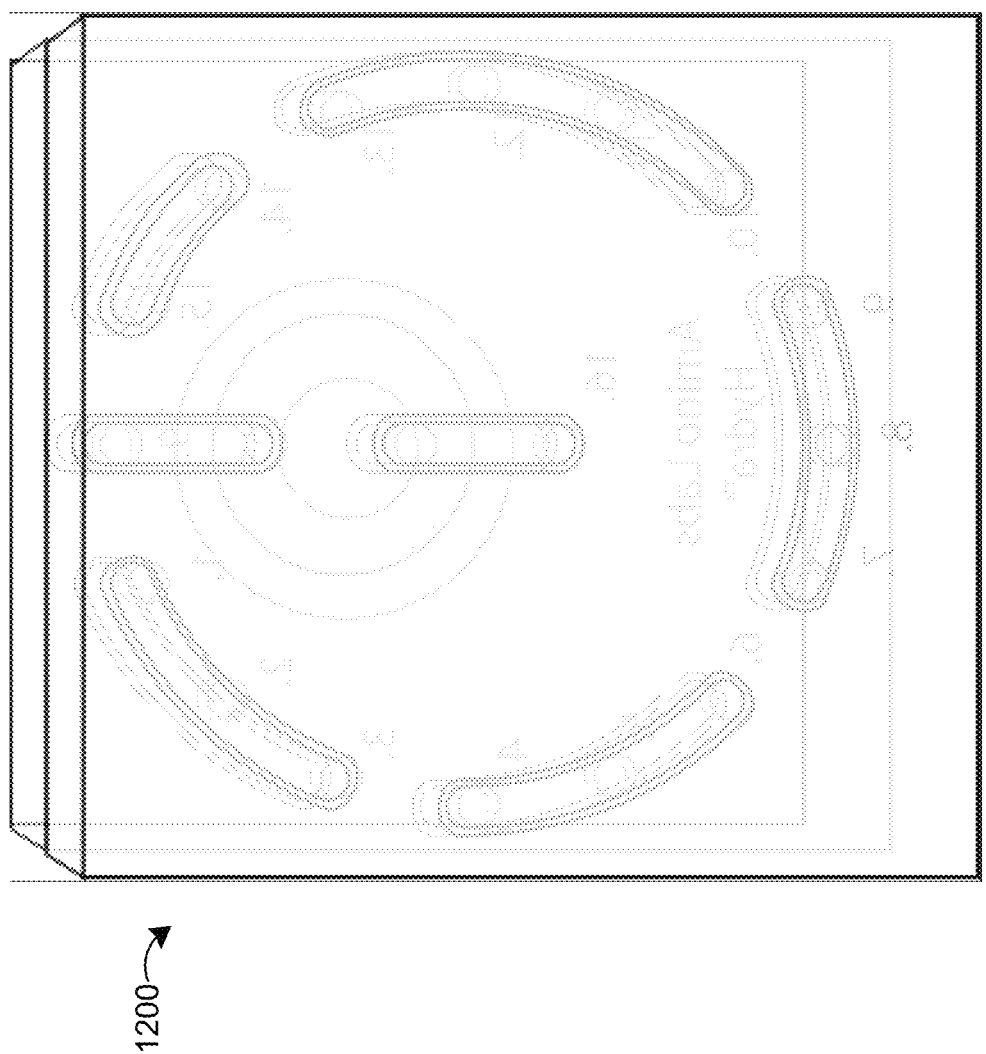

An example of a removable fluidics "chip" 1200 is illustrated in FIGS. 12 and 13 in front and back views, respectively. The module is clear, which allows increased user engagement as the user can view fluids moving through different chambers when operating the machine, and obtain real-time visual feedback regarding fluidic activity as the user presses buttons, etc. to operate the machine. In some embodiments, the fluidics chip could be integrated with a portion of the machine's housing. In some embodiments, the fluidics module could be configured in fun/aesthetic/personalized shapes, such as circles (as shown in FIGS. 12 and 13), words, letters, swirls, mazes, etc., further increasing user engagement.

In one aspect, the various pH chambers, valves and tubing described may be integrated into the afore-mentioned fluidics chip 1200. In another aspect, the fluid pump described may be external to fluidics chip 1200. And in yet another aspect, one or more heaters may be disposed external to the fluidics chip 1200 as well and may be used to heat a portion of or the whole chip, especially if the fluidics chip 1200 is made of a thermally conductive material. The fluidics chip 1200 may be optically transparent or translucent and can be considered in some embodiments as an integrated fluid processing or handling component, manifold or related fluid flow "logic" assembly.

Figure 14:
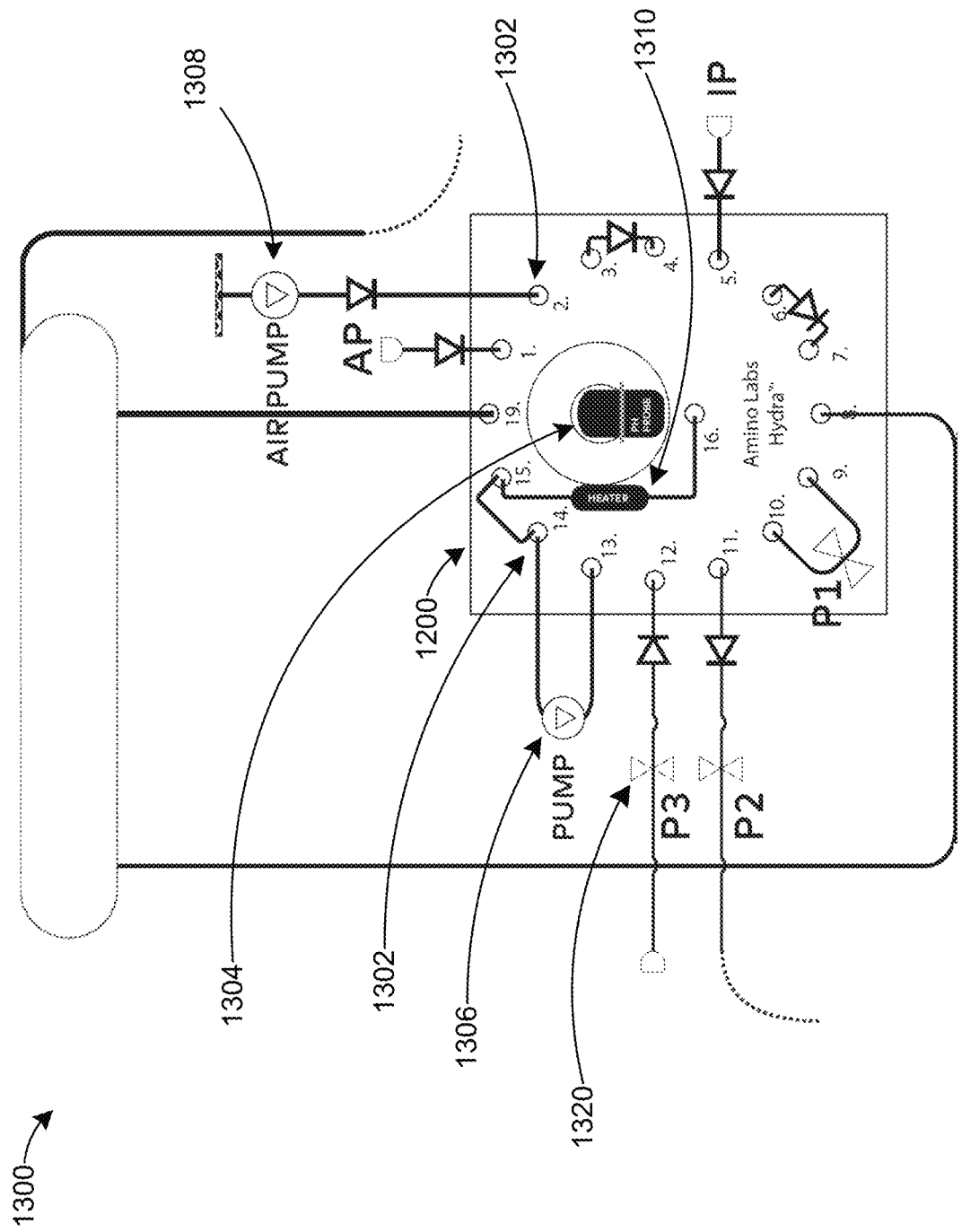
FIG. 14 illustrates exemplary connections to a fluidics chip module.

FIG. 14 illustrates an exemplary fluidics circuit 1300 and associated fluidic accessories including a fluidics chip 1200. The chip is configured and arranged with a plurality of fluid ports 1302 (numbered for example "1" to "19") that can supply or receive/deliver a fluid from/to other components of fluid circuit or system 1300. Therefore, the user can interconnect fluid parts external to the chip 1200 through the ports 1302 as required in a given use instance. As an example, a heater 1310, valve 1320, air pump 1308 and other fluid components, inputs, outputs and associated accessories may be coupled to fluidics chip 1200.

In an exemplary situation as illustrated above, some particular enumerated fluid ports can serve the following purposes: 1. Air inlet, which may comprise a Luer air filter and check valve connected to a pump; 2. Air port inlet with a check valve directing air only in an inwards direction; 3. An output to #4; 4. Check valve from #3; 5. Inoculation inlet with check valve so that an inoculation medium passes only inwardly; 6. Output to #7; 7. Receives flow from #6; 8. Output to reactor input (female Luer); 9. Input from main pinch; 10. Output to main pinch; 11. Disposal outlet port with check valve for outgoing flow only; 12. Feed A inlet with check valve directing flow inwardly only; 13. Inlet from pump; 14. Outlet to pump; 15. Input from heating tube and #16. 16. pH chamber outlet to heating tube; 17. pH outlet to #16; 18. Output to pH chamber; and 19. Input from main reactor.

Figure 15:
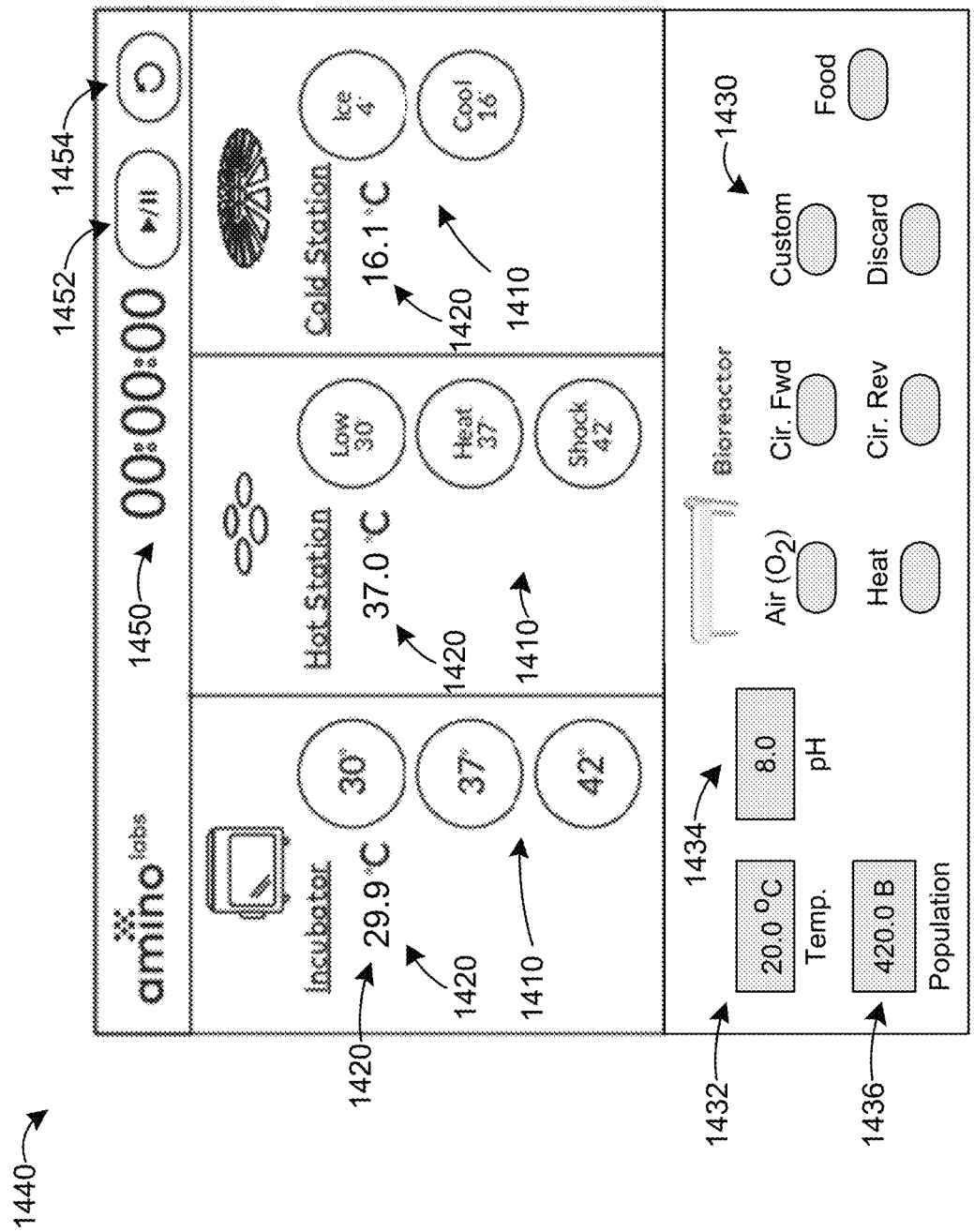
FIG. 15 illustrates a touch screen for the personal laboratory apparatus according to one or more embodiments.

FIG. 15 illustrates a touch screen 1440 for the personal laboratory apparatus according to one or more embodiments. The touch screen 1440 can be the same as or similar to display screens 140, 240. The touch screen 1440 includes controls and real-time display for the incubator, the hot station, the cold station, and the bioreactor. The controls for the incubator, the hot station, and the cold station include touch buttons 1410 that can be pre-programmed for a given temperature setting. For example, the touch buttons 1410 for the incubator and the hot station are pre-programmed for 30° C. (low), 37° C. (heat), and 42° C. (shock). The touch buttons 1410 for the cold station are pre-programmed for 4° C. (ice) and 16° C. (cool). In some embodiments, the user can program the temperature setting for one or more of the touch buttons 1410. The touch buttons 1410 can also be shipped or sold to the customer with the temperature settings pre-programmed. In some embodiments, the touch screen can include touch buttons (e.g., labeled as "+" or "up," and "−" or "down") to incrementally raise or lower the temperature set point for the incubator, the hot station, and/or the cold station. The touch screen 1440 also displays (e.g., in real time) the current temperature of the incubator, the hot station, and the cold station in display field 1420.

In addition, the touch screen 1440 includes controls and displays for the bioreactor. For example, the touch screen 1440 includes control buttons 1430 for introducing air into the bioreactor culture (labeled as "Air (O$_2$)"), heating the bioreactor culture (labeled as "Heat"), setting the circulation direction to forwards or reverse (labeled as "Cir. Fwd" and "Cir. Rev," respectively), discarding some or all of the bioreactor culture (labeled as "Discard"), introducing food into the bioreactor culture (labeled as "Food"), and a custom control. The touch screen 1440 also displays (e.g., in real time) the current temperature 1432 of the bioreactor, the pH 1434, and the microorganism population 1436. In some embodiments, the touch screen can include touch buttons (e.g., as described above) to incrementally raise or lower the temperature set point for the bioreactor.

The touch screen 1440 also includes a timer 1450 with start-stop control 1452 and reset button 1454. The timer 1450 can emit a buzzing sound when the timer has counted down to zero. In addition or in the alternative, the timer 1450 can send a signal to the microcontroller in the apparatus to indicate that the timer has counted down to zero. The microcontroller can then send a signal to a central server, which can cause a text, email message, or other notification to be sent to the user's device or mobile phone.

The touch screen 1440 is in electrical communication with the microcontroller for the personal laboratory apparatus to receive data signals (e.g., temperature, pH, population) that correspond to the display fields 1420, 1432, 1434, 1436. In addition, the touch screen 1440 sends output signals to the microcontroller corresponding to the control buttons (e.g., buttons 1410, 1430) selected by the user. The microcontroller can send control signals to the respective equipment (e.g., incubator) based, at least in part, on the control buttons selected by the user.

Figure 16:
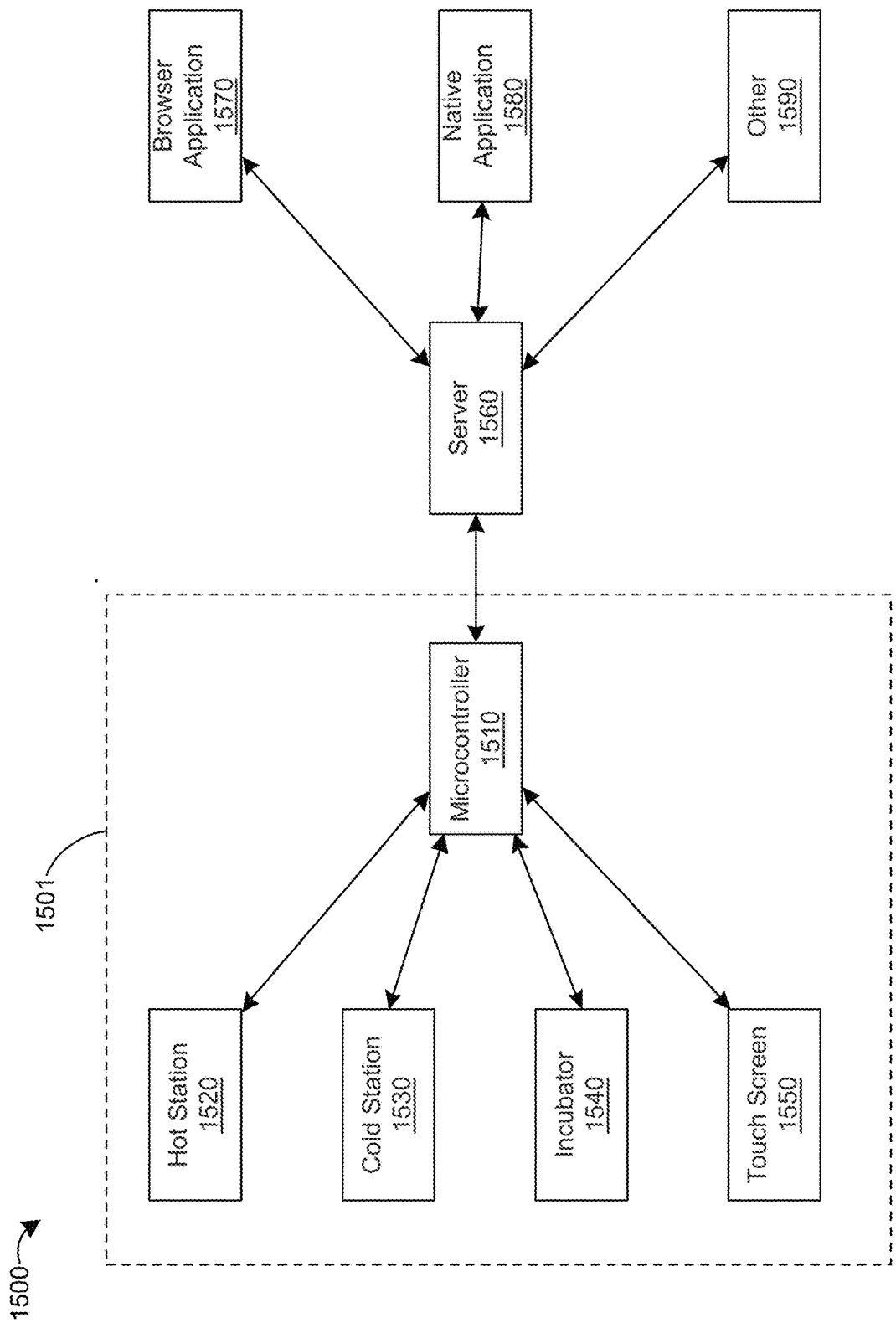
FIG. 16 is a block diagram of the communications systems for personal laboratory apparatus.

FIG. 16 is a block diagram 1500 of the communications systems for personal laboratory apparatus 1501. The personal laboratory apparatus includes a microcontroller 1510 that is in electrical communication with each piece of laboratory equipment including hot station 1520, cold station 1530, and incubator 1540. Through this electrical communication, the microcontroller 1510 can receive data signals from the laboratory equipment and send control signals to the laboratory equipment. For example, the cold station 1530 can send a data signal to the microcontroller 1510 that corresponds to the measured temperature of the cold station 1530 and the actual amount of power being consumed by the cooling elements (e.g., resistance of a thermistor disposed in the cold station 1530). The microcontroller 1510 can determine the measured temperature based on the received data signal (e.g., via a lookup table, a formula, etc.) and then send a control signal to the touch screen 1550 to display (or update the display of) the measured temperature of the cold station 1530. The microcontroller 1510 can also send control signals to the cold station 1530 to adjust the operating power of the cold station 1530 if the measured temperature is greater than a maximum tolerance (e.g., 0.2° C.) from a target temperature. In some embodiments, the microcontroller can compare the measured temperature of each piece of laboratory equipment with a maximum-acceptable temperature. If the measured temperature of a given piece of laboratory equipment (e.g., the incubator 154) is greater than the maximum-acceptable temperature, the microcontroller can cause the laboratory equipment to shut down as a safety feature, for example to prevent overheating.

As discussed above, the touch screen 1550 receives control signals from the microcontroller 1510 to display or update the display of one or more measured operating parameters of each piece of laboratory equipment, such as the measured temperature of the cold station 1530. In addition, the touch screen 1550 sends user input commands to the microcontroller 1510 that correspond to user-controlled inputs (e.g., control buttons as described above with respect to FIG. 15) for the laboratory equipment. For example, the touch screen 1550 can send a user input command to the microcontroller 1510 that corresponds to a new temperature set point for the incubator 1550. The microcontroller 1510 can then modify the control signals to the incubator 1550 to achieve the new temperature set point. In another example, the touch screen 1550 can send a user input command to turn on/off, change the color of, and/or change the intensity of the lights (e.g., LED lights) in one or more pieces of laboratory equipment, such as lights 780 in incubator chamber 740.

FIG. 16 also illustrates that the microcontroller 1510 is in electrical communication (e.g., over a communications network) with a server 1560. The microcontroller 1510 can send data regarding the personal laboratory apparatus 1501 to the server 1560, such as the measured operating parameters of each piece of laboratory equipment (e.g., the measured temperature of cold station 1530) and other data such as when the experiment started, etc. The server 1560 can store, analyze, and/or modify the received data. For example, the server 1560 can store the data in a memory location that the user can access remotely such as through a web browser application 1570 on the user's computer, a native application on the user's computer, or another method 1590 (e.g., social media, text messages, voice messages, and/or other hardware such as but not limited to Arduino, Raspberry Pi, or Little Bits).

The server 1560 can also analyze the data and send commands to the microcontroller to adjust one or more operating parameters of the laboratory equipment (e.g., temperature set point of hot station 1520). In addition, the server 1560 can modify the format of the data (e.g., by generating a graph based on the data) and can generate statistics on the data.

The user can remotely view the touch screen (e.g., touch screen 1440) via the web browser 1570, native application 1580, and/or other method 1590. In addition, the user can virtually press or touch the control buttons on the touch screen to adjust one or more operating conditions of the laboratory equipment on the personal laboratory apparatus 1501. For example, the user can adjust the circulation direction for the bioreactor by virtually pressing on the "Cir. Fwd" or "Cir. Rev" buttons. The server 1560 receives the user's commands and sends them to the microcontroller 1510 to implement.

In some embodiments, standardized wet kits that allow the user to perform particular experiments or procedures are provided. Such "Engineer-it Kits" may include equipment or laboratory hardware supplies such as petri dishes, tubes, and other containers; devices such as "loops" for transferring liquids in controlled, small volumes; supplies such as agar, sterilized water, buffering solutions, cleaning solutions, and so on; and organic materials with which to perform procedures, such as bacterial cells and DNA plasmids. When combined with such kits, the personal laboratory apparatus is intended to provide the user with everything he or she needs in order to carry out procedures and experiments in genetic engineering (except for ordinary household equipment such as a refrigerator and a microwave oven). In contrast to other kits, the "Engineer-it Kits" enable students, for example, to create LB agar plates rather than the teacher completing the task. The kits incorporate a method for safe and simple addition of antibiotics, inducers, and other compounds into the cultures without the need of pipets or scales. By having the Engineer-it Kits include antibiotics, etc. as dissolvable capsules or other vessels, the end user can simply drop a pre-measured capsule into a desired volume of growth media. In an aspect, this avoids the need to perform complicated calculations to determine molar concentrations or dilutions, especially helpful to novice users.

Engineer-it Kits are a base kit that enables users to grow and engineer microorganisms (bacteria and yeast) with DNA plasmids. These are composed of "base kits" where extra add-ons can be included to provide a different end experience. For example, petri dishes, pre-measured LB agar powder, pre-measured sterile water, antibiotics in capsule form, 1 µL and 10 µL inoculating loops, transformation buffer, cells, and recovery media can be the base components. Differing DNA plasmids can be included and the user can complete the exercise with the same base kit. In some instances, inducer (capsule form), metabolic precursors, or specific cell strains may be included.

Engineer-it Kits include "plate stencils" which guide a user through the process of streaking cells. Different streaking methods are graphically displayed on the stencil and the user places the non-selective LB agar plate over top, and then traces a pattern dictated by the stencil.

Figure 17:
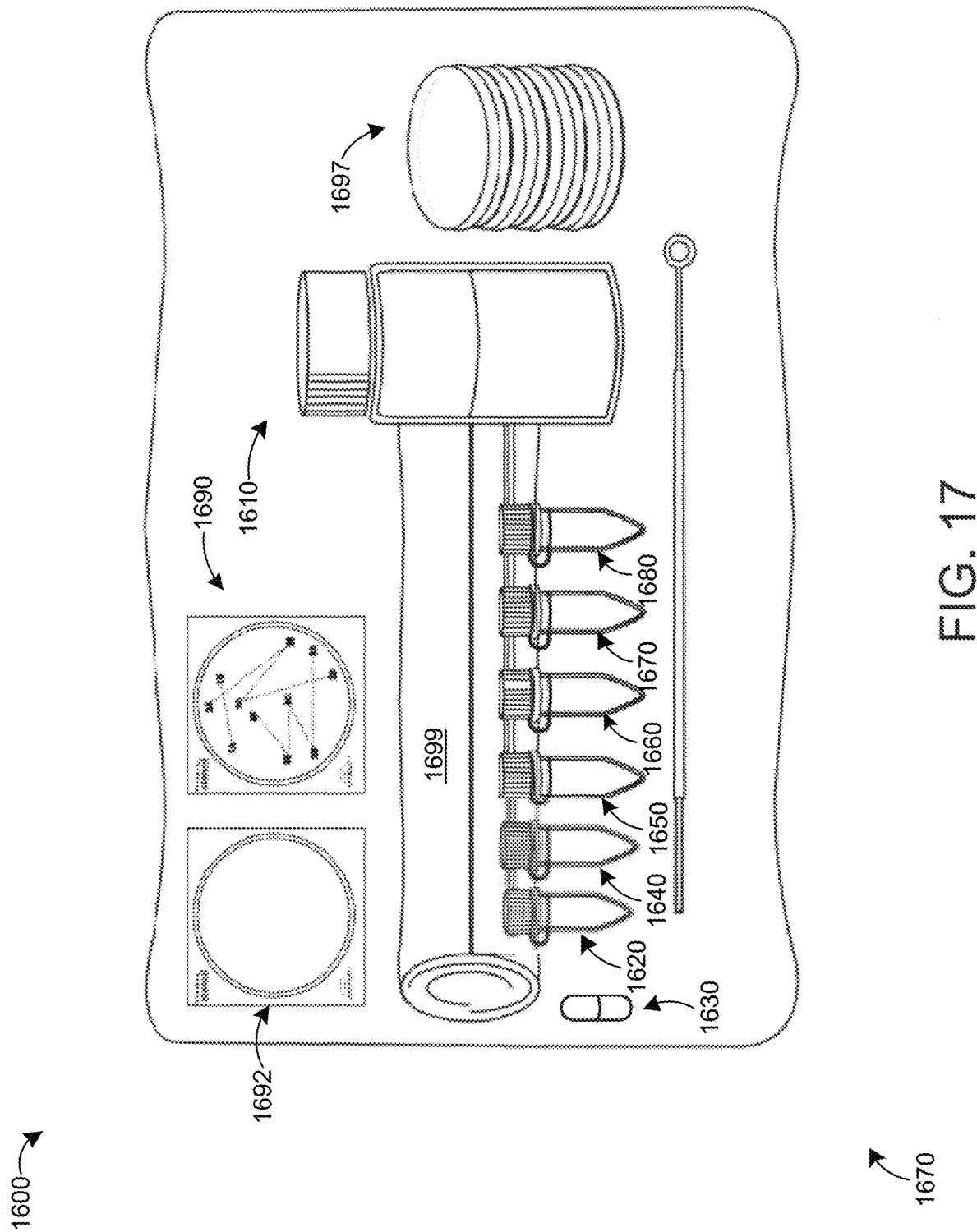
FIG. 17 illustrates a standardized wetware kit for use with the personal laboratory apparatus according to one or more embodiments.

FIG. 17 illustrates a standardized wetware kit 1600 for use with the personal laboratory apparatus according to one or more embodiments. The standardized wetware kit 1600 includes the biological ingredients and associated materials, such as laboratory hardware (e.g., test tubes, petri dishes, inoculation loops, etc.) needed to complete a hands-on genetic engineering experience and experiment. The ingredients as well as the containers that the ingredients are in (e.g. test tubes) are compatible with the laboratory equipment in the personal laboratory apparatus to maximize simplicity and interoperability. The standardized wetware kit 1600, meaning the most commonly-needed ingredients and associated materials can be optimized for used with the personal laboratory apparatus. The components of the standardized wetware kit 1600 for a transformation experiment include (1) a bottle of pre-measured sterile water 1610, (2) a tube of pre-measured growth media powder 1620 (e.g. LB agar), (3) a pre-measured custom pill of selection agent 1630 (e.g. antibiotic), (4) a tube of pre-measured suspended DNA plasmid 1640, (5) a tube of a stab of blank cells 1650, (6) a tube of a stab of positive control cells 1660, (7) a tube of pre-measured transformation or transfection agent 1670 ("T. buffer" and/or water), (8) a pre-measured tube of recovery media 1680, (9) a stencil 1690 for guiding procedures such as "streaking," (10), a second stencil 1692 that the user can draw on to prepare or practice streaking, for example in a canvas kit where the user paints a picture using bacteria, (11) inoculation loops 1695 of 1 µL and 10 µL size, (12) a collection of petri dishes 1697, and (13) an inactivation bag 1699. The standardized wetware kit 1600 components make the methodology standardized, which can enable the use of a software simulator to prepare or guide the non-expert.

The bottle of pre-measured sterile water 1610 is sterile because a non-expert does not have an autoclave or access to an autoclave. The volume of sterile water can be pre-measured at 50 mL or other suitable volume. The total volume of the bottle should be at least five times greater than the volume of water to prevent boil over while the non-expert completes the genetic engineering methodology.

The tube of pre-measured growth media powder 1620 (e.g. LB agar) is of the appropriate mass to be compatible with the volume of sterile water in bottle 1610 to achieve a mixture of 3-4% w/w of LB agar in sterile water. The pre-measured tube growth media powder 1620 enables a non-expert unfamiliar with scientific calculations and w/w concentration, as well as without possession of an accurate scale, to complete the genetic engineering methodology.

The pre-measured custom pill of selection agent 1630 (e.g. antibiotic) is a 100 mg gelatin capsule which contains the appropriate mass selection agent, such as antibiotic, in a filler to enable the selection of a genetically-engineered microorganism. Using the pill 1630 enables a non-expert to add it to the molten LB agar without having to pipet, to calculate molar concentrations, to create stock concentrations, or to work concentrations of the selection agent. The final concentration of selection agent is determined by the pre-measured suspended DNA plasmid and the stab of blank cells in the wetware kit. The pill 1630 can be a size 000 pill in some embodiments.

The tube of pre-measured suspended DNA plasmid 1640 contains DNA and/or nucleic acids that provoke a change in physical traits of the microorganism cultured from the stab of blank cells. A DNA plasmid may have one or more genes or systems of expression that lead to the creation of DNA, RNA, and/or proteins. The DNA is suspended in 25 microliter (µL) or greater volume of buffer to enable a 1 µL inoculation loop to be fully submerged to collect 1 µL of suspended DNA plasmid during the hands-on exercise. Such a methodology means a non-expert can complete the transfer of 1 µL of liquid without the use of a pipet and pipet tips, expensive and complicated-to-use technology.

The tube of a stab of blank cells 1650 includes stab LB agar whereby a non-expert uses a 10 µL inoculation loop to transfer cells to a non-selective LB agar petri dish and subsequently streak cells guided with the stencil 1690. The use of a stab eliminates the need for the non-expert to have to know how to use a pipet to resuspend freeze dried cells.

The tube of a stab of positive control cells 1660 includes stab LB agar whereby a non-expert uses for a 10 µL inoculation loop to transfer cells exhibiting the precise trait, related trait, or the selection marker onto a selective LB agar petri dish. It should be understood that the quantitative values and examples given throughout this disclosure are provided for the sake of illustration and are not limiting. Failure of a genetic-engineering experiment by a non-expert may occur regardless of whether an expert is present or not.

The positive control enables the non-expert to troubleshoot if issues arise. The positive control is also a failsafe to ensure the non-expert gets an outcome from the methodology and remains encouraged.

The tube of pre-measured transformation or transfection agent 1670 ("T. buffer" and/or water) enables the non-expert to facilitate the process of DNA entering into cells. The tube 1670 is compatible with the cold station of the hardware device. The volume of the buffer is also compatible with the depth of the channel of the thermally conductive tube holder. Pre-measured and pre-made T. buffer makes it so the non-expert does not have to complete concentration calculations or perform precise measurement of the components.

The pre-measured tube of recovery media 1680 enables the non-expert to recover cells that have been recently heat shocked so that they recommence growth and normal metabolism. The volume of recovery media is calculated, e.g., 350 microliters (µL), so the non-expert can transfer the right amount of media to the tube of recently engineered cells by tipping rather than using a pipet. The volume of recovery media along with the recipe and volume of the T. buffer were co-developed to be compatible with the depth and thermal transfer constraints of the milled cavities in the thermally conductive tube holder.

The stencil 1690 is a drawing on a piece of substrate such as paper. The stencil 1690 includes three overlapping zig-zags, which is a typical pattern used when streaking cells. Each of the zig zags can be a different color and a numerical system can be used to guide the non-expert through the streaking methodology. The stencil 1690 is designed so the non-selective LB agar petri dish can be placed on top and the non-expert can use the pattern on the stencil as a visual guide and the color difference and numerical system as a procedural guide. In other embodiments, the stencil 1690 can include additional or fewer zigzags, such as 1 zigzag, 2 overlapping zigzags, or 4 or more overlapping zigzags. In some embodiments, 2 overlapping zigzags can be used when streaking cells for "collection."

The inoculation loops 1695 (only one inoculation loop is illustrated in FIG. 17) enable the non-expert to move cells, DNA, buffer and mix samples without the need for a pipet. A 1 microliter (µL) inoculation loop is used for collecting streaked cells an transferring them into the transformation buffer tube. A 1 microliter (µL) inoculation loop is used to transfer DNA from the pre-measured suspended DNA plasmid tube 1640 to the competent cell tube. The 10 microliter (µL) loop is used to transfer cells from stab agar to petri dishes. The 10 microliter (µL) loops are also used for streaking cells. The 10 microliter (µL) loop is also used for spreading engineered cells and positive control cells on LB agar.

The collection of petri dishes 1697 can include 60 mm petri dishes, which are more compatible and appropriate for the dexterity of all audiences, including the small hands of young non-experts, compared to traditional 100 mm petri dishes. The size of the petri dish informs the size of the hardware device incubator station. In addition or in the alternative, the collection of petri dishes 1697 can include 35 mm petri dishes and/or 100 mm petri dishes.

The inactivation bag 1699 is a superior strength, puncture-resistant poly/plastic bag with a heavy-duty zipper that the user can use to collect all the waste and biological material from the experiment/exercise. The user can then pour an inactivation solution (e.g., bleach and water) to inactivate (kill) all biological material in the inactivation bag 1699.

Different variations of ingredients/components of the standardized wetware kit 1600 could be included to change an outcome of a genetic engineering experiment. For example, the pre-measured growth media powder may be LB agar (Miller formulation) or LB agar (Lennox formulation), or the LB agar powder may have further additives or modifications. A further example is that different pre-measured suspended DNA plasmids could be used in place of one another to genetically engineer the cells to exhibit different phenotypes. A further example is that the stab of blank cells could be different strains of microorganisms or different microorganisms. The variations do not disrupt the methodologies of using the standardized wetware kit 1600, enabling a non-expert to repeat the methodologies to gain further experience while observing different genetic engineering outcomes.

Additional ingredients could be added to the standardized wetware kit 1600. In some instances when a DNA plasmid is transformed into a cell, the phenotype requires an external molecule to be added to the system. An example is an inducer whereby gene expression can be activated or inhibited by adding inducer or repressor molecules to the system. Another example is when a cell does not naturally produce, or produces in very low levels, a substrate for an enzymatic reaction or series of enzymatic reactions. A substrate may be added to the standardized wetware kit 1600 to achieve a desirable outcome such as increased enzymatic activity or the enzymatic processing of one molecule into another. The additional ingredients do not disrupt the methodologies of using the standardized wetware kit 1600, and may be used to incrementally advance the hands-on skill level of a non-expert. In some embodiments, the substrate may be volatile. In other embodiments a prolonged release substrate is used. In these situations, the substrate may be embedded in or underneath a layer of an absorbing material that enables controlled release, such as a filter paper disk. The filter paper disk may be placed on the bottom of the petri dish and a molten LB agar layer poured or disposed upon the top of the filter paper. Once the molten LB agar cools and solidifies, the substrate will diffuse out of the material and into the LB agar, ultimately contacting the cells in the petri dish.

In some embodiments, other types of kits that extend the capabilities of the personal laboratory apparatus or provide additional features can be provided. Some of these kits allow the user to create "mementos" from their experimental results. After a user has successfully completed a procedure and has a petri dish with engineered bacteria in it, instead of killing the bacteria and disposing of them, the user can, with a "Keep-it Kit," follow a simple procedure in order to preserve the petri dish with bacteria and keep it as a "trophy." After several successful experiments of engineering bacteria to have different traits, a user can have a collection of successful experiments. After successfully growing genetically-engineered bacteria, a user adds a clear two-part epoxy directly on top of the bacteria until it fully covers. After 24 hours the epoxy becomes hard and seals the plate and bacteria. The petri dish with bacteria under epoxy can be placed in a stand and displayed like a trophy. The Keep-it Kit combines the use of epoxy/resin with a petri-dish containing a user's grown cells or engineered cells. After the epoxy solidifies, the cells are trapped in the petri-dish, preserving them. The preserved cells can be displayed as a trophy and/or demo, and can be used with an included petri dish stand. This kit contrasts with the usual procedure whereby users must inactivate and dispose of their engineered cells. Kit components include a petri dish stand, and an epoxy and resin in separate syringes and/or containers and/or sealed plastic pouches.

Another such kit is the "Print-it Kit." After a user has successfully completed a procedure and has a petri dish of engineered bacteria in it, they can place a piece of paper or fabric on top. After a length of time (which may be several minutes, hours or even up to 24 hours), the object can be removed and the bacteria are transferred onto the object. If the bacteria were engineered to produce a color pigment, the object will also be dyed the color of the bacteria, and the object can serve as a memento.

A similar kit is the "Canvas Kit" which allows a user to "paint with bacteria" on agar petri dishes using the bacteria they engineered.

Another kit is the "Extract-it Kit," which provides a general method to lyse engineered or non-engineered cells cultured on either LB agar or in pelleted form from liquid culture to obtain a sterile cellular extract. Furthermore, the user can use the liquid in a water color pen in order to draw or paint. Extract-it Kit components include a Lysis buffer, lysis accelerator (lysozyme), several test tubes, a 0.22 micrometer (μm) filter, and a syringe.

Aspects of the invention include an "ecosystem" of Hardware, Wetware, and Software. Together these three components provide a comprehensive and intuitive experience. In some embodiments, the invention includes a "Virtual Bioengineer" software simulation that provides a "virtual experience" of using an Engineer-it Kit with the personal laboratory apparatus. Further simulations enable users to learn other bioengineering exercises virtually before they complete the actual hands-on exercises.

Figure 18:
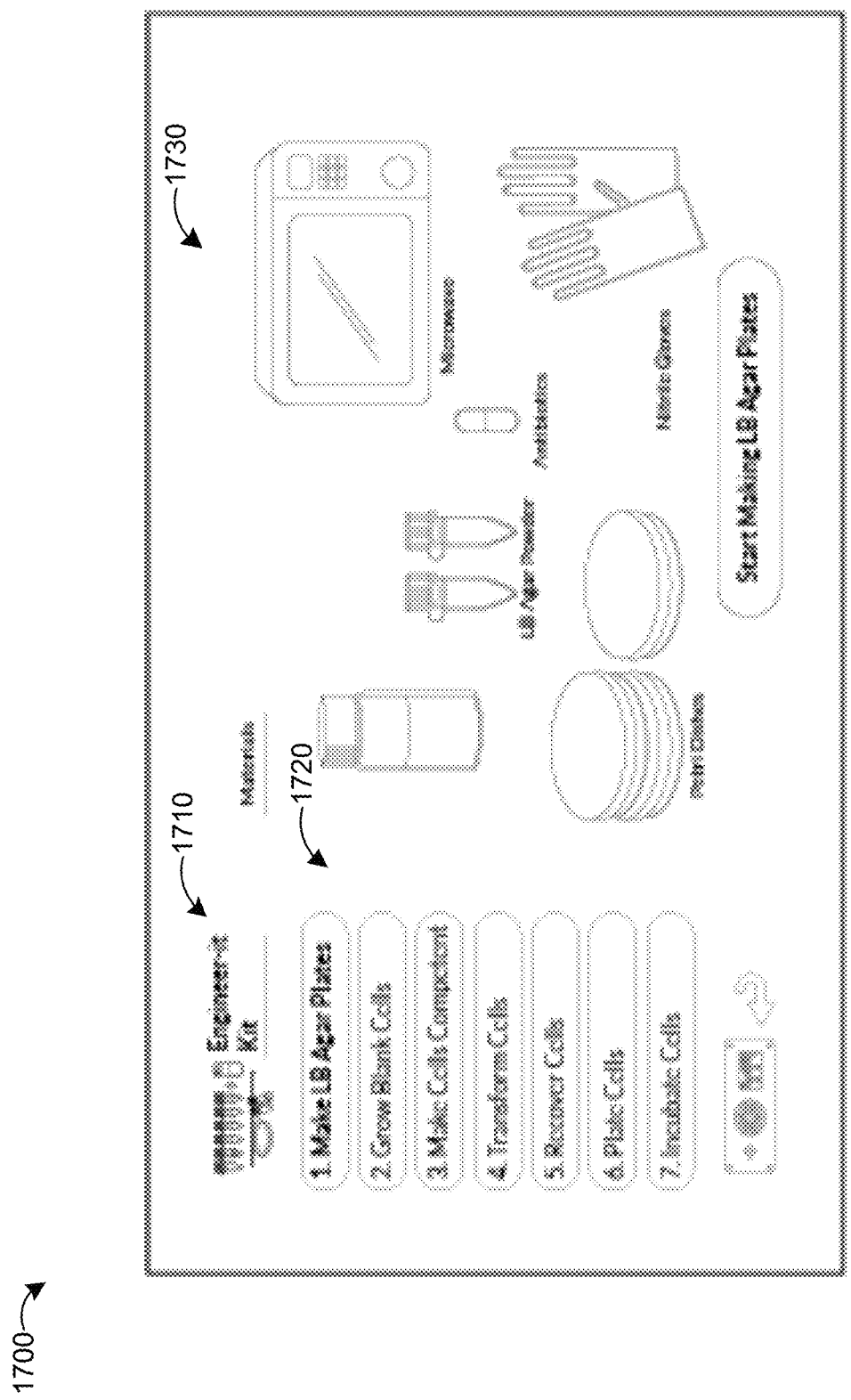
FIG. 18 illustrates an example screenshot from a computer running a Virtual Bioengineer software simulation according to one or more embodiments.
Figure 19:
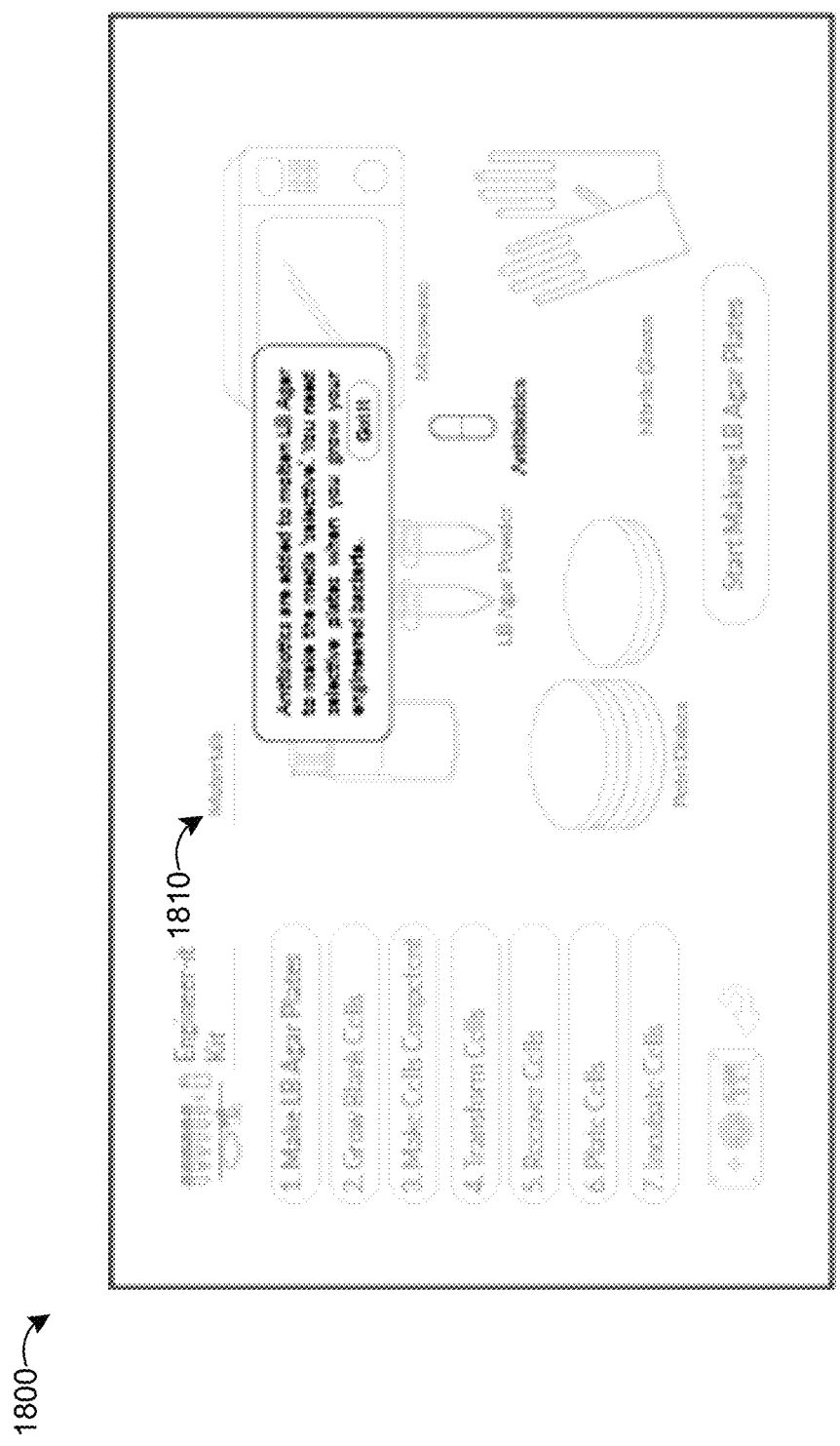
FIG. 19 illustrates an example of a pop-up message in the screenshot illustrated in FIG. 18.

FIG. 18 illustrates an example screenshot 1700 from a computer running the Virtual Bioengineer software simulation according to one or more embodiments. The software simulation can be in the form of the HTML5/Javascript application. The screenshot 1700 includes a title bar 1710 with the wetware kit name to inform the user of which wetware kit to acquire and use, a context bar 1720 that informs the non-expert on the prior, present, and future steps in the experimental method. The user can click on the button under the icons to proceed with the simulation, whereupon the user can virtually perform each of the steps in the given experimental procedure. The software simulation also includes visual assets 1730 that mimic the personal laboratory apparatus (or one or more laboratory equipment contained therein) and wetware kit components (e.g., test tubes, gloves, petri dishes, etc.). In some embodiments, the software simulation includes pop-up messages (e.g., when the mouse is hovered over a visual asset) that provide conceptual information, contextual information, and/or experimental methodology information. An example of a pop-up message 1810 is illustrated in screenshot 1800 in FIG. 19.

Figure 20:
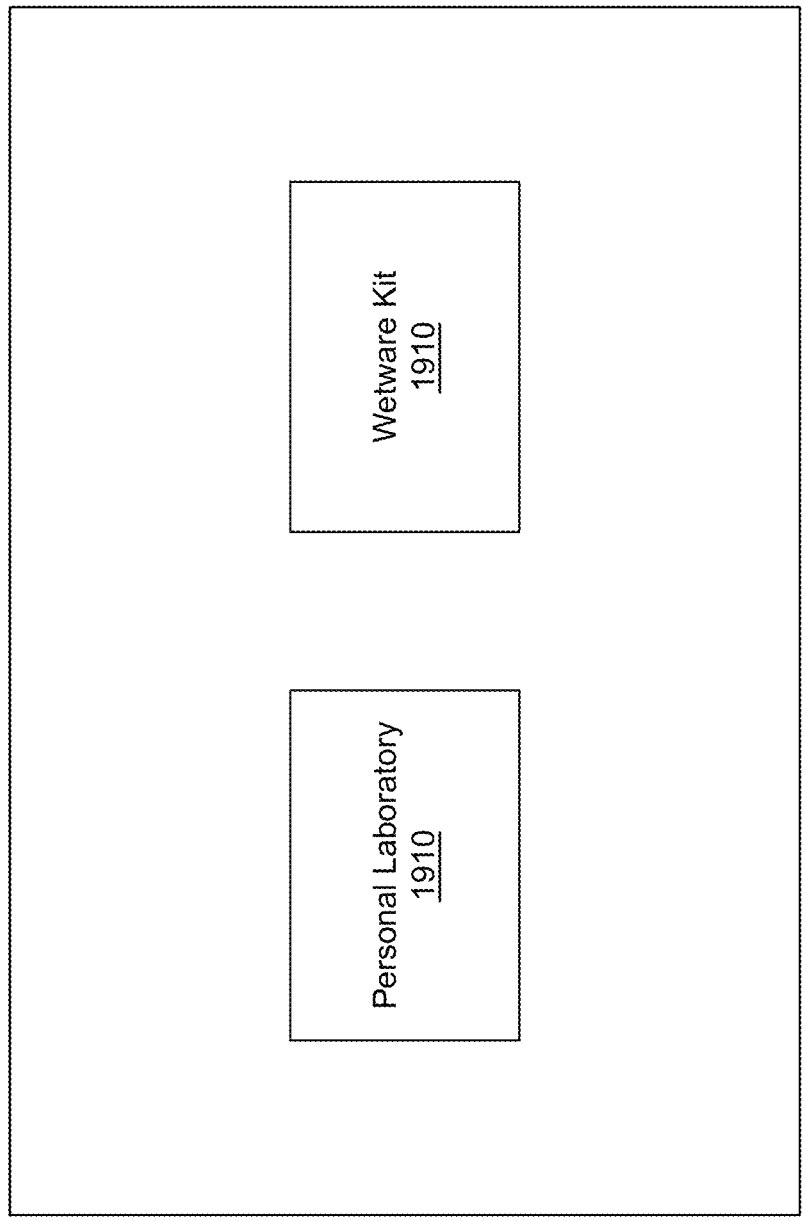
FIG. 20 is a block diagram of a kit according to one or more embodiments.

FIG. 20 is a block diagram of a kit 1900 according to one or more embodiments. The kit 1900 includes a personal laboratory apparatus 1910 and a wetware kit 1920. The personal laboratory apparatus 1910 can be the same as or similar to personal laboratory apparatus 10, 20 described herein. The wetware kit 1920 can be the same as or similar to the standardized wetware kit 1600 described herein. The kit 1900 can be a useful and convenient way to package the personal laboratory apparatus 1910 and wetware kit 1920 for sale. In some embodiments, the standardized wetware kit 1600 can be modified based on the intended end user (e.g., configured for more complicated experiments for more experienced end users and configured for less complicated experiments for less experienced end users).

The personal laboratory apparatus can be configured or extended to produce useful outputs, as opposed to providing educational experiences. One such embodiment is to use the personal laboratory apparatus to produce probiotics. Most probiotics are "freeze dried" and then placed in capsules. Many of the bacteria die in this process. The aim of creating personalized and fresh probiotics not only allows for a personalized approach, but also an effective approach.

The probiotic maker device draws similar principles of a Keurig coffee machine. Within the device there is a bioreactor with various sensors (similar to the educational kits), but may extend to include sensing of other metabolites (e.g., lactate or other) or gases (e.g., oxygen, carbon dioxide, or other). Those skilled in the art will appreciate that the exemplary and illustrative embodiments, including the materials disclosed, quantitative examples and other specifics are dependent on a desired outcome or implementation. Other examples are also equally comprehended by this disclosure and claims, and thus the provided illustrations and numeric ranges are not intended to be limiting.

The device has disposable cartridges or packages of sterile growth media that may function as the primary bioreacting chamber, or that growth media may be transferred into a separate bioreactor chamber.

Once the bioreactor chamber is intact and fastened into the machine, a separate pod, capsule, or other vessel containing a probiotic culture is added. It is possible that the separate pod containing the microorganisms is already in the growth media bag, but only needs to be "popped" to inoculate the culture.

The probiotic culture mixes into the media and the machine incubates at the appropriate temperature, injects filtered gas (if aerobic environment is desired) or not (if anaerobic environment is desired). The sensors which may be in the machine, or may be miniaturized and included in the bag structure, and provide "real-time" feedback about the growth of the microorganisms.

The data that the sensors acquire are analyzed locally and/or in the cloud, or as a collective swarm of probiotic makers, or via a mobile device or computer using artificial intelligence or other computational algorithms. Predetermined experiments allow the inventors to know the growth "signatures" of a healthy culture of growing probiotic bacteria, and such knowledge can be utilized in the analysis of the sensor data. If the sensor data is analyzed as anomalous, or deviates from the "signatures" that are expected, the machine is prompted to dispose of the culture. If the signatures are within a pre-determined range of acceptable values, the culture is "healthy".

After the desired growth period the cells are collected through filtration, centrifugation, or other method. The remaining growth media is disposed of, or further analyzed for safety with the same sensors or other sensors, such as DNA sequencing or other methods.

The collected cells are added to a vessel or many vessels in the correct amount for immediate consumption or consumption within a pre-determined period of time (the time in which they are fresh). The bioreactor is then cleaned and may or may not be disposed of.

Aspects of the invention can also be configured to serve as a machine to produce medicines or useful compounds such as but not limited to flavors, fragrances and vitamins. Distributed, safe, cheap, and abundant medicine is the holy grail for humanity. A machine that can create medicine on demand from natural or genetically-engineered microorganisms is an extension of the use of the technology as a probiotic maker, as described above. The following describes the use of the technology for producing medicines on demand.

Upon collecting cells, they are lysed open (broken open) through some mechanism which may include chemicals, sonic waves, or other. The lysate is then separated into fractions which may include cell debris, DNA, cytoplasmic contents. The cytoplasmic contents are collected and passed through a device that separates the fraction into individual populations of molecules. The device can include a column such as used in high-performance liquid chromatography (i.e., HPLC), or other chromatography. In addition or in the alternative, the device can perform electrophoresis, or other method. During the separation, sensors sending data identify the different fractions so that the user can identify a homogeneous population or heterogeneous populations of interest.

Similar to the above, the "fractionation" device sends data, and using artificial intelligence servers or computers compare known "signatures" that were created from prior experimentation done by the inventors or others. The device collects the desired homogeneous or heterogeneous population of molecules into a vessel that may be used for storage or for human consumption.

Further steps that may or may not be completed by the machine may be required such as mixing the population of molecules with other substances to achieve a desired medical efficacy, stability, or other property. Final analysis of the sample may be completed using sensor devices in the machine or in accompanying machines such as but not limited to absorbance spectroscopy, fluorescence spectroscopy, scanning electron microscopy, Fourier transform infrared spectroscopy, surface plasmon resonance, electrochemistry. All of this sensor data is collected and, through the internet or other communication network, transferred to a centralized server, coupled to a communication and data interface or blockchain system, so that the central system's machines can individually or collectively make decisions about whether the sample is safe for use, and may be implemented as centralized or decentralized architectures.

In some embodiments of the technology, the production of probiotics or medicines may perform the following. During the cell growth stage, the organisms can be "engineered" to secrete the desired molecule into the outer liquid environment. The cells are then pelleted or filtered out and the liquid may or may not be concentrated. The liquid may then be passed through a device that separates the liquid into molecular fractions as described above (like HPLC).

The procedures followed by the technology include safety measures, including data security measures, which are particularly important when producing material to be consumed by humans such as probiotics and medicines. Data may be collected through many sensors. The raw data may or may not be processed in the machine itself. The data can be encrypted or otherwise protected in order to prevent hacking of the system that could allow the creation of "bad microorganisms" or "unsafe medicine/molecules." The encrypted information is passed to another processing entity that can decrypt the information and assess it and compare it to "known signatures," or that can process that information without decrypting it. The machine may be configured to require "commencement" signals every so often as a safety measure. For example, the sensor data must be within a predefined range (the "signature") not only for the end result, but for the entire or segments of the growth cycle. The "signatures" are a discrete stream of signatures from Time=0 to Time=completion. For example, if at hour 12 of incubation, the sensor data is out of range of the "signature" for hour 12 for that particular microorganism, the machine may abort as a safety measure.

These checks would be common for the growth, collection of samples, and the purification and final processing of samples. For a particular medicine there would be an entire "signature" from putting the growth media into the machine, to obtaining the end product. The reproducibility of the system helps to ensure safety.

As an additional security measure, the packaging of reagents and other materials to be used with the apparatus may be constructed so as to protect against people trying to hack the system or create falsified versions. This is similar to how Keurig created proprietary pods, or how printer companies created proprietary ink cartridges, that the relevant machines can sense as being authentic or otherwise. The apparatus may be equipped with sensors that will determine the authenticity of reagents and reject unauthorized/fake versions. In some embodiments, an encrypted key may be used for this purpose. In addition, if sensor data is outside the range of a "signature", as described above, this could provide an additional indication that an inauthentic product was used and thus provide a signal to abort the procedure

Having thus described several aspects and embodiments of the invention, it is to be appreciated that various alterations, modifications, and improvements will readily occur to those of ordinary skill in the art. Such alterations, modifications, and improvements are intended to be within the spirit and scope of the claimed invention. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein.

Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments may be implemented in any of numerous ways. One or more aspects and embodiments of the application involving the performance of processes or methods may utilize program instructions executable by a device (e.g., a computer, a processor, or other device) to perform, or control performance of, the processes or methods.

In this respect, various inventive concepts may be embodied as a computer-readable storage medium (or multiple computer-readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above.

The computer-readable medium or media may be transportable, such that the program or programs stored thereon may be loaded onto one or more different computers or other processors to implement various aspects and embodiments described above. In some embodiments, the computer-readable media may be computer-readable non-transitory media.

The terms "program" and "software" are used herein in a generic sense to refer to any type of computer code or set of computer-executable instructions that may be employed to program a computer or other processor to implement various aspects as described above. Additionally, it should be appreciated that according to one aspect, one or more computer programs, that when executed perform methods as described herein, need not reside on a single computer or processor, but may be distributed in a modular fashion among a number of different computers or processors to implement various aspects and embodiments described above.

Computer-executable instructions may be in many forms, such as program modules, executed by one or more computers or other devices. Generally, program modules include routines, programs, objects, components, data structures, etc. that performs particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code may be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, and/or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that may be used to provide a user interface include printers or display screens for visual presentation of output and speakers or other sound generating devices for audible presentation of output. Examples of input devices that may be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network or the Internet. Such networks may be based on any suitable technology and may operate according to any suitable protocol and may include wireless networks or wired networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The claimed invention should therefore not be considered limited to the particular embodiments described above. Various modifications, equivalent processes, as well as numerous structures to which the claimed invention may be applicable, will be readily apparent to those skilled in the art to which the present technology is directed. The claims are intended to cover such modifications and equivalents.

What is claimed is:

1. A personal laboratory apparatus having multiple multi-use devices for genetic engineering of bacteria or yeast, the apparatus comprising:
a common housing having the multiple multi-use devices for genetic engineering including:
a tube cooling station comprising a plurality of test tube holders each to receive a respective test tube, the tube cooling station maintained at a temperature between about 0° C. and about 17° C.;
a tube heating station comprising a plurality to test tube holders each to receive a respective test tube, the tube heating station maintained at a temperature between about room temperature and about 50° C.;
an incubator, the incubator maintained at a temperature between about room temperature and about 50° C.;
a bioreactor; and
a microcontroller in electrical communication with and for receiving temperature data from the tube cooling station, the tube heating station, the incubator, and the bioreactor, and for sending said temperature data as output signals; and
a touch screen, the touch screen in electrical communication with the microcontroller for receiving the output signals and to display the output signals as the current temperature of each of at least one of the tube cooling station, the tube heating station, the incubator, and the bioreactor, and operative to receive user input as feedback control to the microcontroller for adjusting the current temperature of at least one the cooling station, the heating station, the incubator, and the bioreactor by feedback to the microcontroller,
wherein each of the multiple multi-use devices for genetic engineering are operable to grow and engineer bacteria or yeast simultaneously.

2. The personal laboratory apparatus of claim 1, further comprising a network interface that operably couples the microcontroller to a server.

3. The personal laboratory apparatus of claim 1, further comprising a removable fluidic cartridge that is disposed on or in the common housing and fluidly coupled to the bioreactor.

4. A kit for genetically engineering bacteria or yeast, the kit comprising:
a personal laboratory apparatus having multiple multi-use devices comprising:
a common housing having the multiple multi-use devices disposed on or in the common housing, including:
a tube cooling station comprising a plurality of test tube holders each to receive a respective test tube, the tube cooling station maintained at a temperature between about 0° C. and about 17° C.;
a tube heating station comprising a plurality of test tube holders each to receive a respective test tube, the tube heating station maintained at a temperature between about room temperature and about 50° C.;
an incubator, the incubator maintained at a temperature between about room temperature and about 50° C.;
a bioreactor; and
a microcontroller in electrical communication with and for receiving temperature data from the tube cooling station, the tube heating station, the incubator, and the bioreactor and for sending said temperature data as output signals: and
a touch screen disposed on the common housing, the touch screen in electrical communication with the microcontroller for receiving the output signals and to display the output signals as the current temperature of each of at the least one of the tube cooling station, the tube heating station, the incubator, and the bioreactor, and operative to receive user input as feedback control to the microcontroller for adjusting the current temperature of at least one of the tube cooling station, the tube heating station, the incubator, and the bioreactor by feedback to the microcontroller: and wherein each of the multi-use devices for genetic engineering are operable to grow and engineer bacteria or yeast on; and
a wetware kit comprising laboratory hardware and ingredients for growing and engineering bacteria or yeast on or in the common housing, the wetware kit comprising:
a plurality of test tubes; and
a pre-measured volume or mass of a plurality of bacteria or yeast each pre-measured volume or mass disposed in a corresponding test tube.

5. The kit of claim 4, wherein the wetware kit further comprises: at least one inoculation loop;
a plurality of petri dishes;
a capsule comprising a pre-measured mass of a selection agent; and a stencil configured to guide a streaking procedure.

6. The kit of claim 5, wherein the incubator comprises an incubator chamber sized to receive the petri dishes.

7. The kit of claim 6, wherein the incubator chamber is lockable.

8. The kit of claim 4, wherein the plurality of materials comprises: sterile water;
a growth media;
a suspended DNA plasmid;
a stab of blank cells;
a transformation or transfection agent; and/or a recovery media.

9. The kit of claim 4, wherein the genetic engineering equipment further comprises a network interface that operably couples the microcontroller to a server.

10. The kit of claim 4, wherein the personal laboratory apparatus further comprises a removable fluidic cartridge that is disposed on or in the common housing and fluidly coupled to the bioreactor.

* * * * *